(12) United States Patent
Riley

(10) Patent No.: US 6,509,151 B1
(45) Date of Patent: Jan. 21, 2003

(54) **DNA MOLECULE ENCODING FOR CELLULAR UPTAKE OF *MYCOBACTERIUM TUBERCULOSIS* AND USES THEREOF**

(75) Inventor: Lee W. Riley, New York, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 08/392,210

(22) Filed: Feb. 22, 1995

Related U.S. Application Data

(63) Continuation-in-part of application No. 08/118,442, filed on Sep. 2, 1993, now abandoned.

(51) Int. Cl.[7] ............................. C12Q 1/70; C12Q 1/68; C12N 15/00; C07K 5/00
(52) U.S. Cl. ............................. 435/6; 435/5; 435/7.1; 435/500; 435/320.1; 435/252.3; 530/300
(58) Field of Search ..................... 435/6, 5, 7.1, 500, 435/320.1, 252.3; 530/300

(56) References Cited

U.S. PATENT DOCUMENTS 5,183,737 A   2/1993   Crawford et al.
5,239,066 A   8/1993   Falkow et al.

OTHER PUBLICATIONS

R.R. Isberg, et al., "A Single Genetic Locus Encoded By *Yersinia Pseudotuberculois* Permits Invasion of Cultured Animal Cells By *Escherichia coli* K–12", *Nature*, 317:262–64 (1985).

B. Bloom et al., "Tuberculosis: Commentary on a Reemergent Killer," *Science*, 257:1055–64 (1992).

"Control of Tuberculosis in the United States," *American Thoracic Society*, 146:1623–33 (1992).

F. Laraque et al., "Tuberculosis in HIV–Infected patients," *The AIDS Reader* (Sep./Oct. 1992).

*City Health Information*, vol. II (1992).

Arruda, et al., "Cloning of an *M. tuberculosis* DNA Fragment Associated with Entry and Survival Inside Cells", *Science* 261:1454–1457 (1993).

Arruda, et al., "Cloning of a *Mycobacterium tuberculosis* Gene Necessary for Invasion of Cultured Epithelial Cells", *Abstracts of the General Meeting* 92:41 (1992).

*Primary Examiner*—Kenneth R. Horlick
*Assistant Examiner*—Joyce Tung
(74) *Attorney, Agent, or Firm*—Nixon, Hargrave, Devans & Doyle LLP

(57) ABSTRACT

The present invention relates to a DNA molecule conferring on *Mycobacterium tuberculosis* an ability to enter mammalian cells and to survive within macrophages. The protein encoded by this gene fragment is useful in vaccines to prevent infection by *Mycobacterium tuberculosis*, while the antibodies raised against this protein can be employed in passively immunizing those already infected by the organism. Both these proteins and antibodies may be utilized in diagnostic assays to detect *Mycobacterium tuberculosis* in tissue or bodily fluids. The protein of the present invention can be associated with various other therapeutic materials, for administration to mammals, particularly humans, to achieve uptake of those materials by such cells.

24 Claims, 5 Drawing Sheets

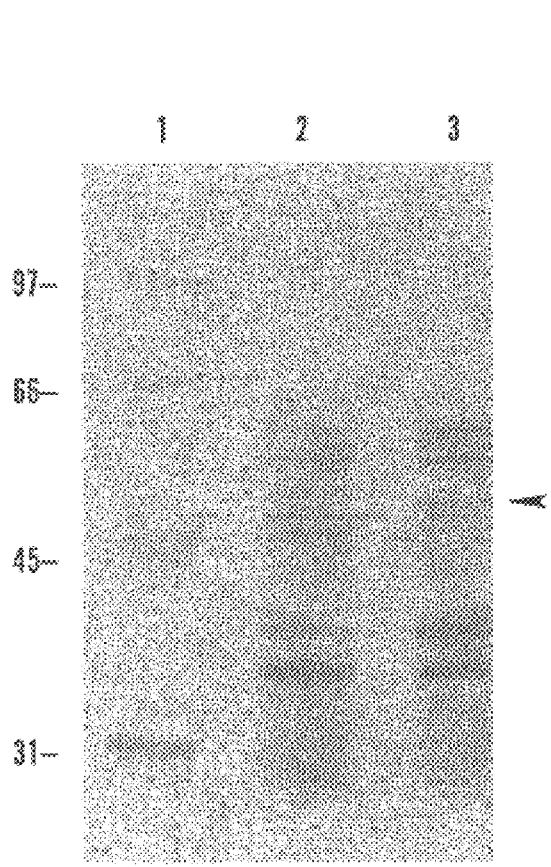
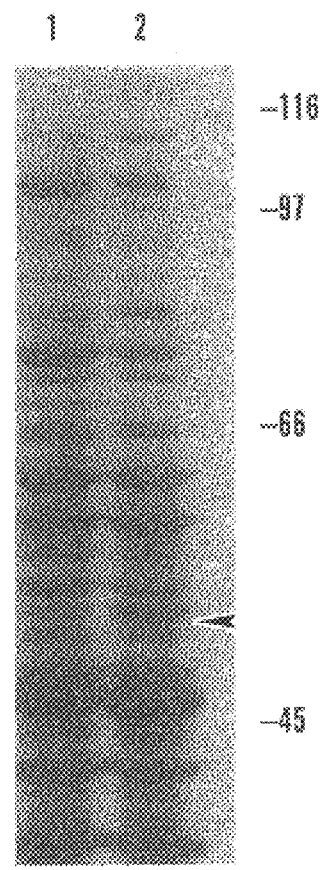
FIG. 3A  FIG. 3B

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 1535 base pairs
      (B) TYPE: nucleic acid
      (C) STRANDEDNESS: double
      (D) TOPOLOGY: unknown (ii) MOLECULE TYPE: DNA (genomic)

(xi) SEQUENCE DESCRIPTION: SEQ ID NO:1:

```
GGATCGAATT GCTGGCCTTT GGCGGGCGAT TCGTGGAGAT CGCCCGTAGA AAGGTTCGCG      60

GACGCCAAGG CCGCCGCAGA CCGCCATAAA CGTAGTTGAC CAGGTGGTCT TGACTGGGGC     120

CGGACACCGA CGTGAACGAG GCGACCCGAT CCGCGTTACA TCCACCTGAT TCCGGCAAAT     180

GTGAACGCCG ACATCAAGGC GACCACGGTG TTCGGCGGTA AGTATGTGTC GTTGACCACG     240

CCGAAAAACC CGACAAAGAG GCGGATAACG CCAAAAGACG TCATCGACGT ACGGTCGGTG     300

ACCACCGAGA TCAACACGTT GTTCCAGACG CTCACCTCGA TCGCCGAGAA GGTGGATCCG     360

GTCAAGCTGA ACCTGACCCT GAGCGCGGCC GCGGAGGCGT TGACCGGGCT GGGCGATAAG     420

TTCGGCGAGT CGATCGTCAA CGCCAACACC GTTCTGGATG ACCTCAATTC GCGGATGCCG     480

CAGTCGCGCC ACGACATTCA GCAATTGGCG GCTCTGGGCG ACGTCTACGC CGACGCGGCG     540

CCGGACCTGT TCGACTTTCT CGACAGTTCG GTGACCACCG CCCGCACCAT CAATGCCCAG     600

CAAGCGGAAC TGGATTCGGC GCTGTTGGCG GCGGCCGGGT TCGGCAACAC CACAGCCGAT     660

GTCTTCGACC GCGGCGGGCC GTATCTGCAG CGGGGGGTCG CCGACCTGGT CCCCACCGCC     720

ACCCTGCTCG ACACTTATAG CCCGGAACTG TTCTGCACGA TCCGCAACTT CTACGATGCC     780

GATCGACCTG ACCGCGGGGC TGCCGCATAG GCCCGGAGTG GTTCGCGATC GGCGAGGCGC     840

ACGTCAAAGT GATTCGCGCC CTTTTTCGCC CACCTGCCCG CCGCGGTGGA TGTGTCCACC     900

CGCCAGGCCG CCGAAGCCGA CCTGGCCGGC AAAGCCGCTC AATATCGTCC CGACGAGCTG     960

GCCCGCTACG CCCAGCGGGT CATGGACTGG CTACACCCCG ACGGCGACCT CACCGACACC    1020

GAACGCGCCC GCAAACGCGG CATCACCCTG AGCAACCAGC AATACGACGG CATGTCACGG    1080
```

```
CTAAGTGGCT ACCTGACCCC CCAAGCGCGG GCCACCTTTG AAGCCGTGCT AGCCAAACTG    1140

GCCGCCCCCG GCGCGACCAA CCCCGACGAC CACACCCCGG TCATCGACAC CACCCCCGAT    1200

GCGGCCGCCA TCGACCGCGA CACCCGCAGC CAAGCCCAAC GCAACCACGA CGGGCTGCTG    1260

GCCGGGCTGC GCGCGCTGAT CCGTCATCCT GCCATCTCGG CCCTCGGCGC CGCCAACTCC    1320

AGGTGCTGTG CGGTCCACGC CGAACGCATG CACGCGATCT CGAATTGGTT GGCACCGTAT    1380

TCGGGATGGA ACTGCTCGAT AGCGATGCCT GCTGCCGTTG CCGCGGCGTT GACATCGCGG    1440

ACGAACGCCT CGTGCTCGAG CACCCCGGCG ACACCGTACT GCGCCCACAG CGTCGAAGGC    1500

AGCCGCTGGC CGTCCGCGTC GACCAAGAGG AATTC                               1535
```

(2) INFORMATION FOR SEQ ID NO:2:

(i) SEQUENCE CHARACTERISTICS:
        (A) LENGTH: 511 amino acids
        (B) TYPE: amino acid
        (D) TOPOLOGY: unknown (ii) MOLECULE TYPE: protein (xi) SEQUENCE DESCRIPTION: SEQ ID NO:2:

```
Gly Ser Asn Cys Trp Pro Leu Ala Gly Asp Ser Trp Arg Ser Pro Val
1               5                   10                  15

Glu Arg Phe Ala Asp Ala Lys Ala Ala Asp Arg His Lys Arg Ser
            20                  25                  30

Xaa Pro Gly Gly Leu Asp Trp Gly Arg Thr Pro Thr Xaa Thr Arg Arg
            35                  40                  45

Pro Asp Pro Arg Tyr Ile His Leu Ile Pro Ala Asn Val Asn Ala Asp
        50                  55                  60

Ile Lys Ala Thr Thr Val Phe Gly Gly Lys Tyr Val Ser Leu Thr Thr
65                  70                  75                  80

Pro Lys Asn Pro Thr Lys Arg Arg Ile Thr Pro Lys Asp Val Ile Asp
                85                  90                  95

Val Arg Ser Val Thr Thr Glu Ile Asn Thr Leu Phe Gln Thr Leu Thr
            100                 105                 110

Ser Ile Ala Glu Lys Val Asp Pro Val Lys Leu Asn Leu Thr Leu Ser
        115                 120                 125

Ala Ala Ala Glu Ala Leu Thr Gly Leu Gly Asp Lys Phe Gly Glu Ser
    130                 135                 140

Ile Val Asn Ala Asn Thr Val Leu Asp Asp Leu Asn Ser Arg Met Pro
145                 150                 155                 160

Gln Ser Arg His Asp Ile Gln Gln Leu Ala Ala Leu Gly Asp Val Tyr
                165                 170                 175

Ala Asp Ala Ala Pro Asp Leu Phe Asp Phe Leu Asp Ser Ser Val Thr
            180                 185                 190

Thr Ala Arg Thr Ile Asn Ala Gln Gln Ala Glu Leu Asp Ser Ala Leu
        195                 200                 205

Leu Ala Ala Ala Gly Phe Gly Asn Thr Thr Ala Asp Val Phe Asp Arg
    210                 215                 220

Gly Gly Pro Tyr Leu Gln Arg Gly Val Ala Asp Leu Val Pro Thr Ala
225                 230                 235                 240

Thr Leu Leu Asp Thr Tyr Ser Pro Glu Leu Phe Cys Thr Ile Arg Asn
                245                 250                 255

Phe Tyr Asp Ala Asp Arg Pro Asp Arg Gly Ala Ala Ala Xaa Ala Arg
            260                 265                 270
```

```
Ser Gly Ser Arg Ser Ala Arg Arg Thr Ser Lys Xaa Phe Ala Pro Phe
        275                 280                 285

Phe Ala His Leu Pro Ala Ala Val Asp Val Ser Thr Arg Gln Ala Ala
    290                 295                 300

Glu Ala Asp Leu Ala Gly Lys Ala Ala Gln Tyr Arg Pro Asp Glu Leu
305                 310                 315                 320

Ala Arg Tyr Ala Gln Arg Val Met Asp Trp Leu His Pro Asp Gly Asp
                325                 330                 335

Leu Thr Asp Thr Glu Arg Ala Arg Lys Arg Gly Ile Thr Leu Ser Asn
            340                 345                 350

Gln Gln Tyr Asp Gly Met Ser Arg Leu Ser Gly Tyr Leu Thr Pro Gln
        355                 360                 365

Ala Arg Ala Thr Phe Glu Ala Val Leu Ala Lys Leu Ala Ala Pro Gly
    370                 375                 380

Ala Thr Asn Pro Asp Asp His Thr Pro Val Ile Asp Thr Thr Pro Asp
385                 390                 395                 400

Ala Ala Ala Ile Asp Arg Asp Thr Arg Ser Gln Ala Gln Arg Asn His
                405                 410                 415

Asp Gly Leu Leu Ala Gly Leu Arg Ala Leu Ile Arg His Pro Ala Ile
            420                 425                 430

Ser Ala Leu Gly Ala Ala Asn Ser Arg Cys Cys Ala Val His Ala Glu
        435                 440                 445

Arg Met His Ala Ile Ser Asn Trp Leu Ala Pro Tyr Ser Gly Trp Asn
    450                 455                 460

Cys Ser Ile Ala Met Pro Ala Val Ala Ala Leu Thr Ser Arg
465                 470                 475                 480

Thr Asn Ala Ser Cys Ser Ser Thr Pro Ala Thr Pro Tyr Cys Ala His
                485                 490                 495

Ser Val Glu Gly Ser Arg Trp Pro Ser Ala Ser Thr Lys Arg Asn
            500                 505                 510

(2) INFORMATION FOR SEQ ID NO:3:

(i) SEQUENCE CHARACTERISTICS:
        (A) LENGTH: 627 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:3:

GTGAACGCCG ACATCAAGGC GACCACGGTG TTCGGCGGTA AGTATGTGTC GTTGACCACG      60

CCGAAAAACC CGACAAAGAG GCGGATAACG CCAAAAGACG TCATCGACGT ACGGTCGGTG     120

ACCACCGAGA TCAACACGTT GTTCCAGACG CTCACCTCGA TCGCCGAGAA GGTGGATCCG     180

GTCAAGCTGA ACCTGACCCT GAGCGCGGCC GCGGAGGCGT TGACCGGGCT GGGCGATAAG     240

TTCGGCGAGT CGATCGTCAA CGCCAACACC GTTCTGGATG ACCTCAATTC GCGGATGCCG     300

CAGTCGCGCC ACGACATTCA GCAATTGGCG GCTCTGGGCG ACGTCTACGC CGACGCGGCG     360

CCGGACCTGT TCGACTTTCT CGACAGTTCG GTGACCACCG CCCGCACCAT CAATGCCCAG     420

CAAGCGGAAC TGGATTCGGC GCTGTTGGCG GCGGCCGGGT TCGGCAACAC CACAGCCGAT     480

GTCTTCGACC GCGGCGGGCC GTATCTGCAG CGGGGGGTCG CCGACCTGGT CCCCACCGCC     540

ACCCTGCTCG ACACTTATAG CCCGGAACTG TTCTGCACGA TCCGCAACTT CTACGATGCC     600

GATCGACCTG ACCGCGGGGC TGCCGCA                                        627
```

(2) INFORMATION FOR SEQ ID NO:4:

(i) SEQUENCE CHARACTERISTICS:
        (A) LENGTH: 209 amino acids
        (B) TYPE: amino acid
        (D) TOPOLOGY: linear (ii) MOLECULE TYPE: peptide (v) FRAGMENT TYPE: unknown (xi) SEQUENCE DESCRIPTION: SEQ ID NO:4:

```
Val Asn Ala Asp Ile Lys Ala Thr Thr Val Phe Gly Gly Lys Tyr Val
1               5                   10                  15

Ser Leu Thr Thr Pro Lys Asn Pro Thr Lys Arg Arg Ile Thr Pro Lys
            20                  25                  30

Asp Val Ile Asp Val Arg Ser Val Thr Thr Glu Ile Asn Thr Leu Phe
            35                  40                  45

Gln Thr Leu Thr Ser Ile Ala Glu Lys Val Asp Pro Val Lys Leu Asn
        50                  55                  60

Leu Thr Leu Ser Ala Ala Ala Glu Ala Leu Thr Gly Leu Gly Asp Lys
65                  70                  75                  80

Phe Gly Glu Ser Ile Val Asn Ala Asn Thr Val Leu Asp Asp Leu Asn
                85                  90                  95

Ser Arg Met Pro Gln Ser Arg His Asp Ile Gln Gln Leu Ala Ala Leu
                100                 105                 110

Gly Asp Val Tyr Ala Asp Ala Ala Pro Asp Leu Phe Asp Phe Leu Asp
            115                 120                 125

Ser Ser Val Thr Thr Ala Arg Thr Ile Asn Ala Gln Gln Ala Glu Leu
        130                 135                 140

Asp Ser Ala Leu Leu Ala Ala Ala Gly Phe Gly Asn Thr Thr Ala Asp
145                 150                 155                 160

Val Phe Asp Arg Gly Gly Pro Tyr Leu Gln Arg Gly Val Ala Asp Leu
                165                 170                 175

Val Pro Thr Ala Thr Leu Leu Asp Thr Tyr Ser Pro Glu Leu Phe Cys
                180                 185                 190

Thr Ile Arg Asn Phe Tyr Asp Ala Asp Arg Pro Asp Arg Gly Ala Ala
            195                 200                 205

Ala
```

(2) INFORMATION FOR SEQ ID NO:5:

(i) SEQUENCE CHARACTERISTICS:
        (A) LENGTH: 650 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:5:

```
GTGGATGTGT CCACCCGCCA GGCCGCCGAA GCCGACCTGG CCGGCAAAGC CGCTCAATAT      60

CGTCCCGACG AGCTGGCCCG CTACGCCCAG CGGGTCATGG ACTGGCTACA CCCCGACGGC     120

GACCTCACCG ACACCGAACG CGCCCGCAAA CGCGGCATCA CCCTGAGCAA CCAGCAATAC     180

GACGGCATGT CACGGCTAAG TGGCTACCTG ACCCCCAAG CGCGGGCCAC CTTTGAAGCC      240

GTGCTAGCCA AACTGGCCGC CCCCGGCGCG ACCAACCCCG ACGACCACAC CCCGGTCATC     300
```

```
GACACCACCC CCGATGCGGC CGCCATCGAC CGCGACACCC GCAGCCAAGC CCAACGCAAC    360

CACGACGGGC TGCTGGCCGG GCTGCGCGCG CTGATCCGTC ATCCTGCCAT CTCGGCCCTC    420

GGCGCCGCCA ACTCCAGGTG CTGTGCGGTC ACGCCGAAC GCATGCACGC GATCTCGAAT     480

TGGTTGGCAC CGTATTCGGG ATGGAACTGC TCGATAGCGA TGCCTGCTGC CGTTGCCGCG    540

GCGTTGACAT CGCGGACGAA CGCCTCGTGC TCGAGCACCC CGGCGACACC GTACTGCGCC    600

CACAGCGTCG AAGGCAGCCG CTGGCCGTCC GCGTCGACCA AGAGGAATTC              650
```

(2) INFORMATION FOR SEQ ID NO:6:

(i) SEQUENCE CHARACTERISTICS:
        (A) LENGTH: 216 amino acids
        (B) TYPE: amino acid
        (D) TOPOLOGY: unknown (ii) MOLECULE TYPE: peptide (xi) SEQUENCE DESCRIPTION: SEQ ID NO:6:

```
Val Asp Val Ser Thr Arg Gln Ala Ala Glu Ala Asp Leu Ala Gly Lys
 1               5                  10                  15

Ala Ala Gln Tyr Arg Pro Asp Glu Leu Ala Arg Tyr Ala Gln Arg Val
                20                  25                  30

Met Asp Trp Leu His Pro Asp Gly Asp Leu Thr Asp Thr Glu Arg Ala
            35                  40                  45

Arg Lys Arg Gly Ile Thr Leu Ser Asn Gln Gln Tyr Asp Gly Met Ser
50                  55                  60

Arg Leu Ser Gly Tyr Leu Thr Pro Gln Ala Arg Ala Thr Phe Glu Ala
65                  70                  75                  80

Val Leu Ala Lys Leu Ala Ala Pro Gly Ala Thr Asn Pro Asp Asp His
                85                  90                  95

Thr Pro Val Ile Asp Thr Thr Pro Asp Ala Ala Ile Asp Arg Asp
                100                 105                 110

Thr Arg Ser Gln Ala Gln Arg Asn His Asp Gly Leu Leu Ala Gly Leu
            115                 120                 125

Arg Ala Leu Ile Arg His Pro Ala Ile Ser Ala Leu Gly Ala Ala Asn
130                 135                 140

Ser Arg Cys Cys Ala Val His Ala Glu Arg Met His Ala Ile Ser Asn
145                 150                 155                 160

Trp Leu Ala Pro Tyr Ser Gly Trp Asn Cys Ser Ile Ala Met Pro Ala
                165                 170                 175

Ala Val Ala Ala Ala Leu Thr Ser Arg Thr Asn Ala Ser Cys Ser Ser
                180                 185                 190

Thr Pro Ala Thr Pro Tyr Cys Ala His Ser Val Glu Gly Ser Arg Trp
            195                 200                 205

Pro Ser Ala Ser Thr Lys Arg Asn
    210                 215
```

(2) INFORMATION FOR SEQ ID NO:7:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

```
GGGGAATTCA TGTGAACGCC GACATCAA                                                    28

(2) INFORMATION FOR SEQ ID NO:8:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

GGGAAGCTTA TTGCGGCAGC CCCGGCGTC                                                   29

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

CGTGAGGGCA TCGAGGTGGC                                                             20

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

GCGTAGGCGT CGGTGACAAA                                                             20
```

DNA MOLECULE ENCODING FOR CELLULAR UPTAKE OF *MYCOBACTERIUM TUBERCULOSIS* AND USES THEREOF

This is a continuation-in-part of U.S. patent application Ser. No. 08/118,442, filed Sep. 2, 1993, now abandoned.

FIELD OF THE INVENTION

The present invention relates to a DNA molecule encoding for uptake of *Mycobacterium tuberculosis* and its use in drugs, vaccines, and diagnostic tests.

BACKGROUND OF THE INVENTION

Tuberculosis is the leading cause of death in the world with an estimated 9 million new cases of tuberculosis and 2.9 million deaths occurring from the disease each year. In the United States, the steadily declining incidents of tuberculosis has been reversed since 1985. This problem is compounded by the increasing incidence of drug-resistant strains of *Mycobacterium tuberculosis*.

Recent outbreaks of tuberculosis have involved settings in which a large number of HIV-infected persons resided in close proximity (e.g., AIDS wards in hospitals, correctional facilities, and hospices). Transmission of tuberculosis to health care workers occurred in these outbreaks; 18 to 50% of such workers showed a conversion in their skin tests. See F. Laraque et. al., "Tuberculosis in HIV-Infected Patients," *The AIDS Reader* (September/October 1992), which is hereby incorporated by reference.

There are two basic clinical patterns that follow infection with *Mycobacterium tuberculosis*.

In the majority of cases, inhaled tubercle bacilli ingested by phagocytic alveolar macrophages are either directly killed or grow intracellularly to a limited extent in local lesions called tubercles. Infrequently in children and immunocompromised individuals, there is early hematogenous dissemination with the formation of small miliary (millet-like) lesions or life-threatening meningitis. More commonly, within 2 to 6 weeks after infection, cell-mediated immunity develops, and infiltration into the lesion of immune lymphocytes and activated macrophages results in the killing of most bacilli and the walling-off of this primary infection, often without symptoms being noted by the infected individual. Skin-test reactivity to a purified protein derivative ("PPD") of tuberculin and, in some cases, X-ray evidence of a healed, calcified lesion provide the only evidence of the infection. Nevertheless, to an unknown extent, dormant but viable *Mycobacterium tuberculosis* bacilli persist.

The second pattern is the progression or breakdown of infection to active disease. Individuals infected with *Mycobacterium tuberculosis* have a 10% lifetime risk of developing the disease. In either case, the bacilli spread from the site of initial infection in the lung through the lymphatics or blood to other parts of the body, the apex of the lung and the regional lymph node being favored sites. Extrapulmonary tuberculosis of the pleura, lymphatics, bone, genito-urinary system, meninges, peritoneum, or skin occurs in about 15% of tuberculosis patients. Although many bacilli are killed, a large proportion of infiltrating phagocytes and lung parenchymal cells die as well, producing characteristic solid caseous (cheese-like) necrosis in which bacilli may survive but not flourish. If a protective immune response dominates, the lesion may be arrested, albeit with some residual damage to the lung or other tissue. If the necrotic reaction expands, breaking into a bronchus, a cavity is produced in the lung, allowing large numbers of bacilli to spread with coughing to the outside. In the worst case, the solid necrosis, perhaps a result of released hydrolases from inflammatory cells, may liquefy, which creates a rich medium for the proliferation of bacilli, perhaps reaching $10^9$ per milliliter. The pathologic and inflammatory processes produce the characteristic weakness, fever, chest pain, cough, and, when a blood vessel is eroded, bloody sputum.

Ignorance of the molecular basis of virulence and pathogenesis is great. It has been suggested that the establishment of molecular evidence regarding a virulent strains, the identification and cloning of putative virulence genes of the pathogen, and the demonstration that virulence can be conveyed to an a virulent strain by those genes is necessary. Although a virulent strains of *Mycobacterium tuberculosis* exist, the nature of the mutations is unknown. Not a single gene involved in the pathogenesis of tuberculosis has been defined in the prior art. The molecular bases of invasion of host cells, intracellular survival, growth, spread, or tissue tropism also have not been known. None of the targets of existing drugs has been characterized at a molecular level, and the mechanism of resistance to any drug has not been defined; no new mycobacterial target for drug development has been characterized in 20 years.

There have been many prescribed treatment regimens for tuberculosis. The regimen recommended by the U.S. Public Health Service and the American Thoracic Society is a combination of isoniazid, rifampicin, and pyrazinamide for two months followed by administration of isoniazid and rifampicin for an additional four months. In persons with HIV infection, isoniazid and rifampicin treatment are continued for an additional seven months. This treatment, called the short-course chemotherapy, produces a cure rate of over 90% for patients who complete it. Treatment for multi-drug resistant tuberculosis requires addition of ethambutol and/or streptomycin in the initial regimen, or second line drugs, such as kanamycin, amikacin, capreomycin, ethionamide, cyclcoserine, PAS, and clofazimin. New drugs, such as ciprofloxacin and ofloxacin can also be used. For individuals infected with conventional *Mycobacterium tuberculosis* and showing PPD positive results, chemoprophylaxis with isoniazid has been about 90% effective in preventing the disease. Tuberculosis and these treatments are discussed in more detail in B. Bloom et. al., "Tuberculosis: Commentary on a Reemergent Killer," *Science*, 257:1055–64 (1992); "Control of Tuberculosis in the United States," *American Thoracic Society*, 146:1623–33 (1992); *City Health Information*, vol. 11 (1992), which is hereby incorporated by reference.

Although the currently used treatments for tuberculosis have a relatively high level of success, the need remains to improve the success rate for treating this disease. Moreover, in view of the ever-increasing level of *Mycobacterium tuberculosis* strains which are resistant to conventional treatment regimens, new types of treatment must be developed. In high tuberculosis endemic areas, both in the United States and abroad, such resistant strains are becoming increasingly present.

SUMMARY OF THE INVENTION

The present invention relates to isolated DNA molecules conferring on *Mycobacterium tuberculosis* an ability to enter mammalian cells and/or to survive within macrophages as well as isolated proteins or polypeptides encoded by those isolated DNA molecules. The molecules can be inserted as heterologous DNA in an expression vector forming a recombinant DNA expression system for producing the proteins or peptides. Likewise, the heterologous DNA, usually inserted in an expression vector to form a recombinant DNA expression system can be incorporated in a cell to achieve this objective.

The isolated proteins or polypeptides of the present invention can be combined with a pharmaceutically-acceptable carrier to form a vaccine or used alone for administration to mammals, particularly humans, for preventing infection by *Mycobacterium tuberculosis*. Alternatively, each of the proteins or polypeptides of the present invention can be used to raise an antibody or a binding portion thereof. The antibody or binding portion thereof may be used alone or combined with a pharmaceutically-acceptable carrier to treat mammals, particularly humans, already exposed to *Mycobacterium tuberculosis* to induce a passive immunity to prevent disease occurrence.

The proteins or polypeptides of the present invention or the antibodies or binding portions thereof raised against them can also be utilized in a method for detection of *Mycobacterium tuberculosis* in a sample of tissue or body fluids. When the proteins or polypeptides are utilized, they are provided as an antigen. Any reaction with the antigen or the antibody is detected using an assay system which indicates the presence of *Mycobacterium tuberculosis* in the sample. Alternatively, *Mycobacterium tuberculosis* can be detected in such a sample by providing a nucleotide sequence of the gene conferring on *Mycobacterium tuberculosis* an ability to enter mammalian cells and/or to survive within macrophages or a fragment thereof as a probe in a nucleic acid hybridization assay or a gene amplication detection procedure (e.g., using a polymerase chain reaction procedure). Any reaction with the probe is detected so that the presence of *Mycobacterium tuberculosis* in the sample is indicated.

The proteins or polypeptides of the present invention can also be used for purposes unrelated to the treatment or detection of *Mycobacterium tuberculosis* . More particularly, the ability of those proteins or polypeptides to confer on *Mycobacterium tuberculosis* an ability to enter mammalian cells can be utilized to permit such cells to uptake other materials. This can be achieved with a product that includes a material for uptake by mammalian cells and the proteins or polypeptides of the present invention associated with that material.

Isolation of the DNA molecules of the present invention constitutes a significant advance in the treatment and detection of such bacteria. It also provides the basis for a vaccine to prevent infection by *Mycobacterium tuberculosis* and a pharmaceutical agent for passive immunization for those exposed to *Mycobacterium tuberculosis*. The proteins utilized in the vaccine or to produce the pharmaceutical agent can be produced at high levels using recombinant DNA technology.

In diagnostic applications, the proteins or polypeptides of the present invention as well as antibodies and binding portions thereof against them permit rapid determination of whether a particular individual is infected with *Mycobacterium tuberculosis* . Moreover, such detection can be carried out without requiring an examination of the individual being tested for an antibody response.

Aside from the development of treatments and diagnostic tools for *Mycobacterium tuberculosis* , the present invention's ability to confer entry of such organisms into mammalian cells has significant utility in therapeutic treatments requiring the introduction of materials into cells, particularly to macrophages. By associating the protein or polypeptide of the present invention with pharmaceutical agents, such agents can be rapidly introduced into cells for treatment thereof. The enhanced cellular uptake of such products can reduce drug dosages, thus reducing toxicity and cost. For example, in conventional cancer treatment, drug toxicity is a major problem due to the requirement for administration of large dosages; the present invention has the potential to reduce such high dosage levels while enabling delivery of equivalent or higher drug levels intracellularly.

Furthermore, binding the proteins or polypeptides of the present invention to DNA fragments can be utilized in conjunction with gene therapy regimens. In particular, the ability of the encoded product of the DNA molecules of the present invention to augment uptake into macrophages provides an opportunity to deliver genes specifically to macrophages. Such a system can be used to induce not only humoral immunity but cell-mediated immunity.

BRIEF DESCRIPTION OF THE DRAWINGS

FIGS. 3A, 3B, and 3C are thin-section electron micrographs of human macrophages exposed to the invasive recombinant *E. coli* clone XL1-Blue(pZX7) for 3 hours (FIG. 3A) and 24 hours (FIG. 3B) compared with cells exposed to nonpathogenic *E. coli* XL1-Blue (pBluescript) for 24 hours (FIG. 3C). The bacteria become compartmentalized, surrounded by layers of membrane inside the macrophage (FIG. 3B). No bacteria were visible after 24 hours by electron microscopy in macrophages exposed to XL1-Blue(pBluescript). The bars represent 1 $\mu$m.

FIGS. 6A and B show a transmission electron microscopy study of the association of latex beads coated with the *Mycobacterium tuberculosis* invasion-association recombinant protein with HeLa cells. FIG. 6A shows recombinant protein-coated beads (arrow). FIG. 6B shows control *E. coli* lysate protein-coated beads (arrow).

DETAILED DESCRIPTION OF THE INVENTION

Figure 1:
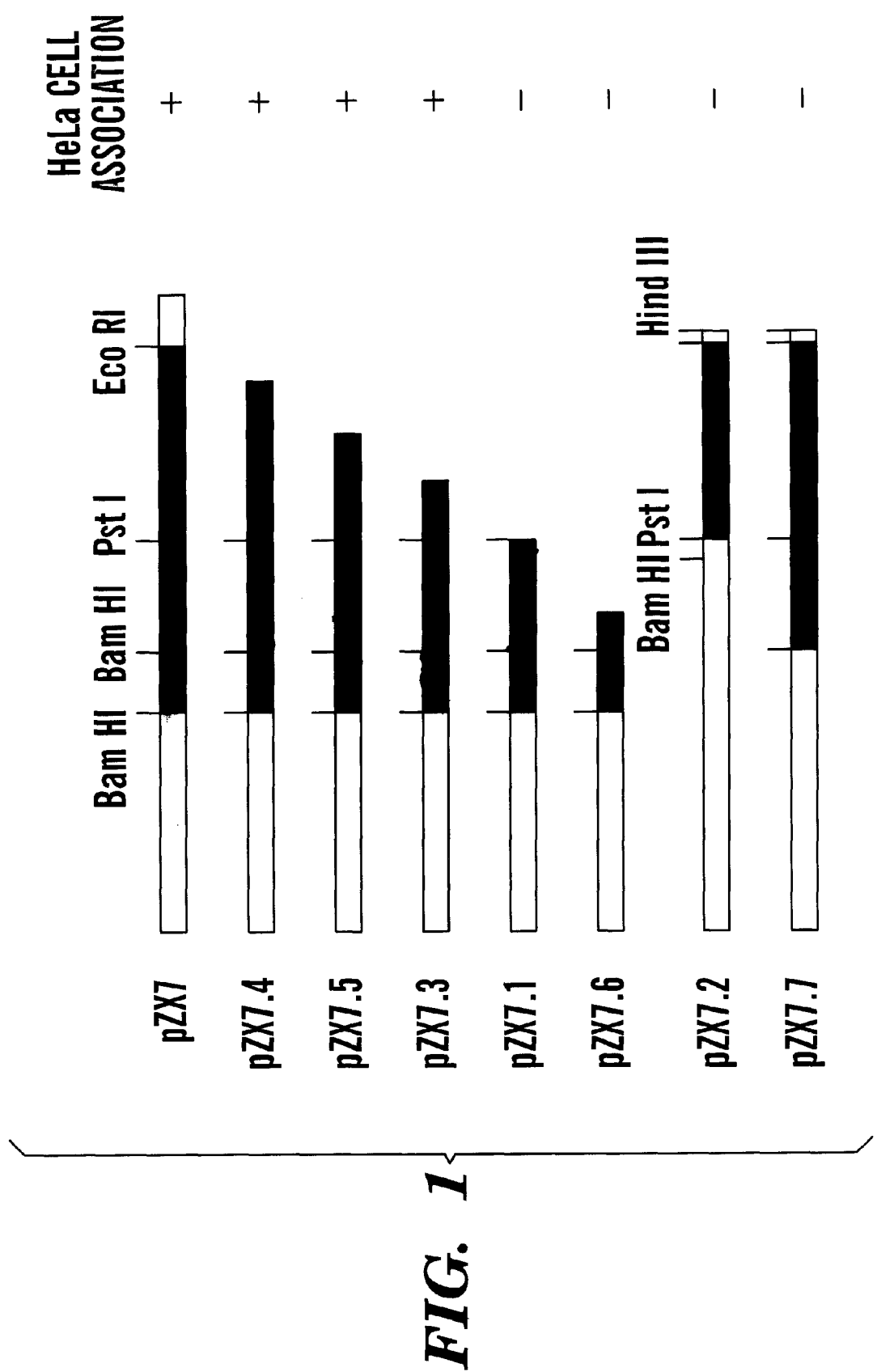
FIGS. 1A, 1B, and 1C are thin-section electron micrographs of HeLa cells infected with *Mycobacterium tuberculosis* strain, including H37Ra (ATCC25177) (FIG. 1A), and the invasive recombinant strain *E. coli* XL1-Blue (pZX7) (FIGS. 1B and 1C). An electron-transparent zone surrounds the *Mycobacterium tuberculosis* organism (arrow in FIG. 1A). The cells were incubated with *Mycobacterium tuberculosis* strain for 72 hours in FIG. 1A and with XL1-Blue (pZX7) for 7.5 hours in FIGS. 1B and 1C. Multiple organisms are visible in FIG. 1C, suggesting bacterial proliferation inside phagosomes. The bars represent 0.5 $\mu$m.

One aspect of the present invention relates to an isolated DNA molecule conferring on *Mycobacterium tuberculosis* an ability to enter mammalian cells and to survive within macrophages. This DNA molecule comprises the nucleotide sequence corresponding to SEQ. ID. No. 1 as follows:

```
GGATCGAATT GCTGGCCTTT GGCGGGCGAT TCGTGGAGAT CGCCCGTAGA AAGGTTCGCG    60
GACGCCAAGG CCGCCGCAGA CCGCCATAAA CGTAGTTGAC CAGGTGGTCT TGACTGGGGC   120
CGGACACCGA CGTGAACGAG GCGACCCGAT CCGCGTTACA TCCACCTGAT TCCGGCAAAT   180
GTGAACGCCG ACATCAAGGC GACCACGGTG TTCGGCGGTA AGTATGTGTC GTTGACCACG   240
CCGAAAAACC CGACAAAGAG GCGGATAACG CCAAAAGACG TCATCGACGT ACGGTCGGTG   300
ACCACCGAGA TCAACACGTT GTTCCAGACG CTCACCTCGA TCGCCGAGAA GGTGGATCCG   360
GTCAAGCTGA ACCTGACCCT GAGCGCGGCC GCGGAGGCGT TGACCGGGCT GGGCGATAAG   420
TTCGGCGAGT CGATCGTCAA CGCCAACACC GTTCTGGATG ACCTCAATTC GCGGATGCCG   480
CAGTCGCGCC ACGACATTCA GCAATTGGCG GCTCTGGGCG ACGTCTACGC CGACGCGGCG   540
CCGGACCTGT TCGACTTTCT CGACAGTTCG GTGACCACCG CCCGCACCAT CAATGCCCAG   600
CAAGCGGAAC TGGATTCGGC GCTGTTGGCG GCGGCCGGGT TCGGCAACAC CACAGCCGAT   660
GTCTTCGACC GCGGCGGGCC GTATCTGCAG CGGGGGGTCG CCGACCTGGT CCCCACCGCC   720
ACCCTGCTCG ACACTTATAG CCCGGAACTG TTCTGCACGA TCCGCAACTT CTACGATGCC   780
GATCGACCTG ACCGCGGGGC TGCCGCATAG GCCCGGAGTG GTTCGAGATC GGCGAGGCGC   840
ACGTCAAAGT GATTCGCGCC CTTTTTCGCC CACCTGCCCG CCGCGGTGGA TGTGTCCACC   900
CGCCAGGCCG CCGAAGCCGA CCTGGCCGGC AAAGCCGCTC AATATCGTCC CGACGAGCTG   960
GCCCGCTACG CCCAGCGGGT CATGGACTGG CTACACCCCG ACGGCGACCT CACCGACACC  1020
GAACGCGCCC GCAAACGCGG CATCACCCTG AGCAACCAGC AATACGACGG CATGTCACGG  1080
CTAAGTGGCT ACCTGACCCC CCAAGCGCGG GCCACCTTTG AAGCCGTGCT AGCCAAACTG  1140
GCCGCCCCCG GCGCGACCAA CCCCGACGAC CACACCCCGG TCATCGACAC CACCCCCGAT  1200
GCGGCCGCCA TCGACCGCGA CACCCGCAGC AAGCCCAAC GCAACCACGA CGGGCTGCTG  1260
GCCGGGCTGC GCGCGCTGAT CCGTCATCCT GCCATCTCGG CCCTCGGCGC CGCCAACTCC  1320
AGGTGCTGTG CGGTCCACGC CGAACGCATG CACGCGATCT CGAATTGGTT GGCACCGTAT  1380
TCGGGATGGA ACTGCTCGAT AGCGATGCCT GCTGCCGTTG CCGCGGCGTT GACATCGCGG  1440
ACGAACGCCT CGTGCTCGAG CACCCCGGCG ACACCGTACT GCGCCCACAG CGTCGAAGGC  1500
AGCCGCTGGC CGTCCGCGTC GACCAAGAGG AATTC                             1535
```

The above DNA molecule encodes for a polypeptide having a molecular weight of about 50 to 55 kilodaltons, preferably 52 kilodaltons. The amino acid sequence, deduced from the nucleotide sequence corresponding to SEQ. ID. No. 1, represents a highly hydrophilic protein with a hydrophobic region at its carboxy terminus. It could be a secreted protein, a cytoplasmic protein, or a surface protein with its carboxy terminus attached to the outer membrane of the organism. It is believed that this protein or polypeptide has the deduced amino acid sequence corresponding to SEQ. ID. No. 2 as follows:

```
Gly Ser Asn Cys Trp Pro Leu Ala Gly Asp Ser Trp Arg Ser Pro Val
1               5                   10                  15

Glu Arg Phe Ala Asp Ala Lys Ala Ala Ala Asp Arg His Lys Arg Ser
            20              25                  30

Xaa Pro Gly Gly Leu Asp Trp Gly Arg Thr Pro Thr Xaa Thr Arg Arg
        35                  40                  45

Pro Asp Pro Arg Tyr Ile His Leu Ile Pro Ala Asn Val Asn Ala Asp
    50                  55                  60

Ile Lys Ala Thr Thr Val Phe Gly Gly Lys Tyr Val Ser Leu Thr Thr
65                  70                  75                  80

Pro Lys Asn Pro Thr Lys Arg Arg Ile Thr Pro Lys Asp Val Ile Asp
                85                  90                  95

Val Arg Ser Val Thr Thr Glu Ile Asn Thr Leu Phe Gln Thr Leu Thr
                100                 105                 110

Ser Ile Ala Glu Lys Val Asp Pro Val Lys Leu Asn Leu Thr Leu Ser
            115                 120                 125

Ala Ala Ala Glu Ala Leu Thr Gly Leu Gly Asp Lys Phe Gly Glu Ser
        130                 135                 140

Ile Val Asn Ala Asn Thr Val Leu Asp Asp Leu Asn Ser Arg Met Pro
145                 150                 155                 160

Gln Ser Arg His Asp Ile Gln Gln Leu Ala Ala Leu Gly Asp Val Tyr
                165                 170                 175

Ala Asp Ala Ala Pro Asp Leu Phe Asp Phe Leu Asp Ser Ser Val Thr
            180                 185                 190

Thr Ala Arg Thr Ile Asn Ala Gln Gln Ala Glu Leu Asp Ser Ala Leu
        195                 200                 205

Leu Ala Ala Ala Gly Phe Gly Asn Thr Thr Ala Asp Val Phe Asp Arg
    210                 215                 220

Gly Gly Pro Tyr Leu Gln Arg Gly Val Ala Asp Leu Val Pro Thr Ala
225                 230                 235                 240

Thr Leu Leu Asp Thr Tyr Ser Pro Glu Leu Phe Cys Thr Ile Arg Asn
                245                 250                 255

Phe Tyr Asp Ala Asp Arg Pro Asp Arg Gly Ala Ala Ala Xaa Ala Arg
            260                 265                 270

Ser Gly Ser Arg Ser Ala Arg Arg Thr Ser Lys Xaa Phe Ala Pro Phe
        275                 280                 285

Phe Ala His Leu Pro Ala Ala Val Asp Val Ser Thr Arg Gln Ala Ala
    290                 295                 300

Glu Ala Asp Leu Ala Gly Lys Ala Ala Gln Tyr Arg Pro Asp Glu Leu
305                 310                 315                 320

Ala Arg Tyr Ala Gln Arg Val Met Asp Trp Leu His Pro Asp Gly Asp
                325                 330                 335

Leu Thr Asp Thr Glu Arg Ala Arg Lys Arg Gly Ile Thr Leu Ser Asn
            340                 345                 350

Gln Gln Tyr Asp Gly Met Ser Arg Leu Ser Gly Tyr Leu Thr Pro Gln
        355                 360                 365

Ala Arg Ala Thr Phe Glu Ala Val Leu Ala Lys Leu Ala Ala Pro Gly
    370                 375                 380
```

```
Ala Thr Asn Pro Asp Asp His Thr Pro Val Ile Asp Thr Thr Pro Asp
385                 390                 395                 400

Ala Ala Ala Ile Asp Arg Asp Thr Arg Ser Gln Ala Gln Arg Asn His
                405                 410                 415

Asp Gly Leu Leu Ala Gly Leu Arg Ala Leu Ile Arg His Pro Ala Ile
            420                 425                 430

Ser Ala Leu Gly Ala Ala Asn Ser Arg Cys Cys Ala Val His Ala Glu
        435                 440                 445

Arg Met His Ala Ile Ser Asp Trp Leu Ala Pro Tyr Ser Gly Trp Asn
    450                 455                 460

Cys Ser Ile Ala Met Pro Ala Ala Val Ala Ala Ala Leu Thr Ser Arg
465                 470                 475                 480

Thr Asn Ala Ser Cys Ser Ser Thr Pro Ala Thr Pro Tyr Cys Ala His
            485                 490                 495

Ser Val Glu Gly Ser Arg Trp Pro Ser Ala Ser Thr Lys Arg Asn
            500                 505                 510
```

In the immediately-preceding sequence, Xaa signifies a stop codon. Production of this isolated protein or polypeptide is preferably carried out using recombinant DNA technology. The protein or polypeptide is believed to have one or more antigenic determinants conferring on *Mycobacterium tuberculosis* an ability to enter mammalian cells and to survive within macrophages.

As indicated by the presence of the stop codons in above SEQ. ID. Nos. 1 and 2, these sequences constitute or are encoded by several open reading frames. The first open reading frame extends from position 181 to position 807 of the nucleotide sequence of SEQ. ID. No. 1. This sequence which confers an ability to enter mammalian cells has the following nucleotide sequence (SEQ. ID. No. 3):

```
GTGAACGCCG ACATCAAGGC GACCACGGTG TTCGGCGGTA AGTATGTGTC GTTGACCACG   60
CCGAAAAACC CGACAAAGAG GCGGATAACG CCAAAAGACG TCATCGACGT ACGGTCGGTG  120
ACCACCGAGA TCAACACGTT GTTCCAGACG CTCACCTCGA TCGCCGAGAA GGTGGATCCG  180
GTCAAGCTGA ACCTGACCCT GAGCGCGGCC GCGGAGGCGT TGACCGGGCT GGGCGATAAG  240
TTCGGCGAGT CGATCGTCAA CGCCAACACC GTTCTGGATG ACCTCAATTC GCGGATGCCG  300
CAGTCGCGCC ACGACATTCA GCAATTGGCG GCTCTGGGCG ACGTCTACGC CGACGCGGCG  360
CCGGACCTGT TCGACTTTCT CGACAGTTCG GTGACCACCG CCCGCACCAT CAATGCCCAG  420
CAAGCGGAAC TGGATTCGGC GCTGTTGGCG GCGGCCGGGT TCGGCAACAC CACAGCCGAT  480
GTCTTCGACC GCGGCGGGCC GTATCTGCAG CGGGGGGTCG CCGACCTGGT CCCCACCGCC  540
ACCCTGCTCG ACACTTATAG CCCGGAACTG TTCTGCACGA TCCGCAACTT CTACGATGCC  600
GATCGACCTG ACCGCGGGGC TGCCGCA                                     627
```

The nucleotide sequence corresponding to SEQ. ID. No. 3 encodes for the following amino acid sequence (SEQ. ID. No. 4):

```
Val Asn Ala Asp Ile Lys Ala Thr Thr Val Phe Gly Gly Lys Tyr Val
1               5                   10                  15
Ser Leu Thr Thr Pro Lys Asn Pro Thr Lys Arg Arg Ile Thr Pro Lys
            20                  25                  30
Asp Val Ile Asp Val Arg Ser Val Thr Thr Glu Ile Asn Thr Leu Phe
            35                  40                  45
Gln Thr Leu Thr Ser Ile Ala Glu Lys Val Asp Pro Val Lys Leu Asn
        50                  55                  60
Leu Thr Leu Ser Ala Ala Ala Glu Ala Leu Thr Gly Leu Gly Asp Lys
65                  70                  75                  80
Phe Gly Glu Ser Ile Val Asn Ala Asn Thr Val Leu Asp Asp Leu Asn
                85                  90                  95
Ser Arg Met Pro Gln Ser Arg His Asp Ile Gln Gln Leu Ala Ala Leu
                100                 105                 110
Gly Asp Val Tyr Ala Asp Ala Ala Pro Asp Leu Phe Asp Phe Leu Asp
            115                 120                 125
Ser Ser Val Thr Thr Ala Arg Thr Ile Asn Ala Gln Gln Ala Glu Leu
        130                 135                 140
Asp Ser Ala Leu Leu Ala Ala Ala Gly Phe Gly Asn Thr Thr Ala Asp
145                 150                 155                 160
Val Phe Asp Arg Gly Gly Pro Tyr Leu Gln Arg Gly Val Ala Asp Leu
                165                 170                 175
Val Pro Thr Ala Thr Leu Leu Asp Thr Tyr Ser Pro Glu Leu Phe Cys
                180                 185                 190
Thr Ile Arg Asn Phe Tyr Asp Ala Asp Arg Pro Asp Arg Gly Ala Ala
            195                 200                 205
Ala
```

The protein or polypeptide encoded by this amino acid sequence has one or more antigenic determinants conferring on *Mycobacterium tuberculosis* an ability to enter mammalian cells. This protein or polypeptide has a molecular weight of 22–28 kilodaltons, preferably 25 kilodaltons.

The sequences corresponding to SEQ. ID. Nos. 1 and 2 contain or are encoded by an additional open reading frame which is believed to confer on *Mycobacterium tuberculosis* an ability to survive within macrophages. The nucleotide sequence corresponding to this open reading frame is as follows (SEQ. ID. No. 5):

```
GTGGATGTGT CCACCCGCCA GGCCGCCGAA GCCGACCTGG CCGGCAAAGC CGCTCAATAT   60
CGTCCCGACG AGCTGGCCCG CTACGCCCAG CGGGTCATGG ACTGGCTACA CCCCGACGGC  120
GACCTCACCG ACACCGAACG CGCCCGCAAA CGCGGCATCA CCCTGCGCAA CCAGCAATAC  180
GACGGCATGT CACGGCTAAG TGGCTACCTG ACCCCCCAAG CGCGGGCCAC CTTTGAAGCC  240
GTGCTAGCCA AACTGGCCGC CCCCGGCGCG ACCAACCCCG ACGACCACAC CCCGGTCATC  300
GACACCACCC CCGATCGGGC CGCCATCGAC CGCGACACCC GCAGCCAAGC CCAAGCGAAC  360
CACGACGGGC TGCTGGCCGG GCAGCGCGCG CTGATCCGTC ATCCTGCCAT CTCGGCCCTC  420
GGCGCCGCCA ACTCCAGGTC CTGTGCGGTC CACGCCGAAC GCATGCACGC GATCTCGAAT  480
TGGTTGGCAC CGTATTCGGG ATGGAACTGC TCGATAGCGA TGCCTGCTGC CGTTGCCGCG  540
GCGTTGACAT CGCGGACGAA CGCCTCGTGC TCGAGCACCC CGGCGACACC GTACTGCGCC  600
CACAGCGTCG AAGGCAGCCG CTGGCCGTCC GCGTCGACCA AGAGGAATTC            650
```

The nucleotide sequence corresponding to SEQ. ID. No. 5 encodes for a protein or polypeptide having the following amino acid sequence (SEQ. ID. No. 6):

```
Val Asp Val Ser Thr Arg Gln Ala Ala Glu Ala Asp Leu Ala Gly Lys
1             5                   10                  15

Ala Ala Gln Tyr Arg Pro Asp Glu Leu Ala Arg Tyr Ala Gln Arg Val
            20              25              30

Met Asp Trp Leu His Pro Asp Gly Asp Leu Thr Asp Thr Glu Arg Ala
        35              40              45

Arg Lys Arg Gly Ile Thr Leu Ser Asn Gln Gln Tyr Asp Gly Met Ser
    50                  55                  60

Arg Leu Ser Gly Tyr Leu Thr Pro Gln Ala Arg Ala Thr Phe Glu Ala
65                  70                  75                  80

Val Leu Ala Lys Leu Ala Ala Pro Gly Ala Thr Asn Pro Asp Asp His
            85              90                      95

Thr Pro Val Ile Asp Thr Thr Pro Asp Ala Ala Ala Ile Asp Arg Asp
            100             105                 110

Thr Arg Ser Gln Ala Gln Arg Asn His Asp Gly Leu Leu Ala Gly Leu
        115                 120             125

Arg Ala Leu Ile Arg His Pro Ala Ile Ser Ala Leu Gly Ala Ala Asn
    130             135                 140

Ser Arg Cys Cys Ala Val His Ala Glu Arg Met His Ala Ile Ser Asn
145             150                 155                     160

Trp Leu Ala Pro Tyr Ser Gly Trp Asn Cys Ser Ile Ala Met Pro Ala
            165                 170                 175

Ala Val Ala Ala Ala Leu Thr Ser Arg Thr Asn Ala Ser Cys Ser Ser
            180             185                 190

Thr Pro Ala Thr Pro Tyr Cys Ala His Ser Val Glu Gly Ser Arg Trp
        195             200                 205

Pro Ser Ala Ser Thr Lys Arg Asn
    210                 215
```

The putative protein or polypeptide conferring on *Mycobacterium tuberculosis* an ability to survive within macrophages has a predicted molecular weight of at least 21 kilodaltons. It is expected that in nature this protein or polypeptide has a weight greater than the 21 kilodaltons of SEQ. ID. No. 6, because SEQ. ID. No. 6 is encoded by a DNA molecule with no stop codon at its terminus. See SEQ. ID. No. 5. Therefore, in nature, the protein or polypeptide conferring survival within macrophages is believed to be longer.

The proteins or polypeptides of the present invention are preferably produced in purified form by conventional techniques. For instance, see Examples 5–6 infra. To isolate the proteins, the *E. coli* host cell carrying a recombinant plasmid is propagated, homogenized, and the homogenate is centrifuged to remove bacterial debris. The supernatant is then subjected to sequential ammonium sulfate precipitation. The fraction containing the proteins of the present invention are subjected to gel filtration in an appropriately sized dextran or polyacrylamide column to separate the proteins. If necessary, the protein fraction may be further purified by HPLC.

Any one of the DNA molecules conferring on *Mycobacterium tuberculosis* an ability to enter mammalian cells and/or to survive within macrophages can be incorporated in cells using conventional recombinant DNA technology. Generally, this involves inserting the selected DNA molecule into an expression system to which that DNA molecule is heterologous (i.e. not normally present). The heterologous DNA molecule is inserted into the expression system or vector in proper orientation and correct reading frame. The vector contains the necessary elements for the transcription and translation of the inserted protein-coding sequences.

U.S. Pat. No. 4,237,224 to Cohen and Boyer, which is hereby incorporated by reference, describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture.

Recombinant genes may also be introduced into viruses, such as vaccina virus. Recombinant viruses can be generated by transfection of plasmids into cells infected with virus.

Suitable vectors include, but are not limited to, the following viral vectors such as lambda vector system gtll, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK +/− or KS +/− (see "Stratagene Cloning Systems" Catalog (1993) from Stratagene, La Jolla, Calif., which is hereby incorporated by reference), pQE, pIH821, pGEX, pET series (see F. W. Studier et. al., "Use of T7 RNA Polymerase to Direct Expression of Cloned Genes," *Gene Expression Technology* vol. 185 (1990), which is hereby incorporated by reference) and any derivatives thereof. Recombinant molecules can be introduced into cells via transformation, particularly transduction, conjugation, mobilization, or electroporation. The DNA sequences are cloned into the vector using standard cloning procedures in the art, as described by Maniatis et al., *Molecular Cloning: A Laboratory Manual*, Cold Springs Laboratory, Cold Springs Harbor, N.Y. (1982), which is hereby incorporated by reference.

A variety of host-vector systems may be utilized to express the protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus). The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA (mRNA) translation).

Transcription of DNA is dependent upon the presence of a promotor which is a DNA sequence that directs the binding of RNA polymerase and thereby promotes mRNA synthesis. The DNA sequences of eucaryotic promoters differ from those of procaryotic promoters. Furthermore, eucaryotic promoters and accompanying genetic signals may not be recognized in or may not function in a procaryotic system, and, further, procaryotic promoters are not recognized and do not function in eucaryotic cells.

Similarly, translation of mRNA in procaryotes depends upon the presence of the proper procaryotic signals which differ from those of eucaryotes. Efficient translation of mRNA in procaryotes requires a ribosome binding site called the Shine-Dalgarno (SD) sequence on the mRNA. This sequence is a short nucleotide sequence of mRNA that is located before the start codon, usually AUG, which encodes the amino-terminal methionine of the protein. The SD sequences are complementary to the 3'- end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology*, 68:473 (1979), which is hereby incorporated by reference.

Promotors vary in their "strength" (i.e. their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in *E. coli*, its bacteriophages, or plasmids, promoters such as the T7 phage promoter, lac promoter, trp promoter, recA promoter, ribosomal RNA promoter, the $P_R$ and $P_L$ promotors of coliphage lambda and others, including but not limited, to lacUV5, ompF, bla, lpp, and the like, may be used to direct high levels of transcription of adjacent DNA segments. Additionally, a hybrid trp-lacUV5 (tac) promotor or other *E. coli* promoters produced by recombinant DNA or other synthetic DNA techniques may be used to provide for transcription of the inserted gene.

Bacterial host cell strains and expression vectors may be chosen which inhibit the action of the promotor unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in procaryotic cells. These transcription and translation initiation signals may vary in "strength" as measured by the quantity of gene specific messenger RNA and protein synthesized, respectively. The DNA expression vector, which contains a promotor, may also contain any combination of various "strong" transcription and/or translation initiation signals. For instance, efficient translation in *E. coli* requires a Shine-Dalgarno (SD) sequence about 7–9 bases 5' to the initiation codon (ATG) to provide a ribosome binding site. Thus, any SD-ATG combination that can be utilized by host cell ribosomes may be employed. Additionally, any SD-ATG combination produced by recombinant DNA or other techniques involving incorporation of synthetic nucleotides may be used.

Once the desired isolated DNA molecule conferring on *Mycobacterium tuberculosis* an ability to enter mammalian cells and/or to survive within macrophages has been cloned into an expression system, it is ready to be incorporated into a host cell. Such incorporation can be carried out by the various forms of transformation noted above, depending upon the vector/host cell system. Suitable host cells include, but are not limited to, bacteria, virus, yeast, mammalian cells, and the like.

Generally, the human immune system responds to infection by pathogenic bacteria by producing antibodies that bind to specific proteins or carbohydrates on the bacterial surface. The antibodies stimulate binding to macrophages which have receptors that bind to the Fc region of the antibodies. Other serum proteins, called complement, coat the foreign particle and stimulate their ingestion by binding to specific surface receptors on the macrophage. Once the particle is bound to the surface of the macrophage, the sequential process of ingestion begins by continual apposition of a segment of the plasma membrane to the particle surface. Surface receptors on the membranes then interact with ligands distributed uniformity over the particle surface to link the surfaces together. The macrophage enveloping the particle is then delivered to lysosomes where the particle is ingested.

Some organisms are ingested (i.e. undergo uptake) by macrophages but are not killed. Amongst these is *Mycobacterium tuberculosis* . As a result, such organisms are able to survive indefinitely within macrophages and, when they escape from the macrophage, cause active tuberculosis.

In view of the present invention's determination of nucleotide sequences conferring on *Mycobacterium tuberculosis* an ability to enter mammalian cells, the molecular basis for *Mycobacterium tuberculosis* uptake is suggested. With this information and the above-described recombinant DNA technology, a wide array of therapeutic and/or prophylatic agents and diagnostic procedures for, respectively, treating and detecting *Mycobacterium tuberculosis* can be developed.

For example, an effective amount of the proteins or polypeptides of the present invention can be administered alone or in combination with a pharmaceutically-acceptable carrier to humans, as a vaccine, for preventing infection by *Mycobacterium tuberculosis*. Alternatively, it is possible to administer to individuals exposed to *Mycobacterium tuberculosis* an effective amount of an antibody or binding portion thereof against these proteins or polypeptides as a passive immunization. Such antibodies or binding portions thereof are administered alone or in combination with a pharmaceutically-acceptable carrier to effect short term treatment of individuals who may have been recently exposed to *Mycobacterium tuberculosis* .

Antibodies suitable for use in inducing passive immunity can be monoclonal or polyclonal.

Monoclonal antibody production may be effected by techniques which are well-known in the art. Basically, the process involves first obtaining immune cells (lymphocytes) from the spleen of a mammal (e.g., mouse) which has been previously immunized with the antigen of interest (i.e. the protein or peptide of the present invention) either in vivo or in vitro. The antibody-secreting lymphocytes are then fused with (mouse) myeloma cells or transformed cells, which are capable of replicating indefinitely in cell culture, thereby producing an immortal, immunoglobulin-secreting cell line. The resulting fused cells, or hybridomas, are cultured and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler and Milstein, *Nature* 256:495 (1975), which is hereby incorporated by reference.

Mammalian lymphocytes are immunized by in vivo immunization of the animal (e.g., a mouse) with one of the proteins or polypeptides of the present invention. Such immunizations are repeated as necessary at intervals of up to several weeks to obtain a sufficient titer of antibodies. The virus is carried in appropriate solutions or adjuvants. Following the last antigen boost, the animals are sacrificed and spleen cells removed.

Fusion with mammalian myeloma cells or other fusion partners capable of replicating indefinitely in cell culture is effected by standard and well-known techniques, for example, by using polyethylene glycol (PEG) or other fusing agents (See Milstein and Kohler, *Eur. J. Immunol.* 6:511 (1976), which is hereby incorporated by reference). This immortal cell line, which is preferably murine, but may also be derived from cells of other mammalian species, including but not limited to rats and humans, is selected to be deficient in enzymes necessary for the utilization of certain nutrients, to be capable of rapid growth and to have good fusion capability. Many such cell lines are known to those skilled in the art, and others are regularly described.

Procedures for raising polyclonal antibodies are also well known. Typically, such antibodies can be raised by administering one of the proteins or polypeptides of the present invention subcutaneously to New Zealand white rabbits which have first been bled to obtain pre-immune serum. The antigens can be injected at a total volume of 100 μl per site at six different sites. Each injected material will contain synthetic surfactant adjuvant pluronic polyols, or pulverized acrylamide gel containing the protein or polypeptide after SDS-polyacrylamide gel electrophoresis. The rabbits are then bled two weeks after the first injection and periodically boosted with the same antigen three times every six weeks. A sample of serum is then collected 10 days after each boost. Polyclonal antibodies are then recovered from the serum by affinity chromatography using the corresponding antigen to capture the antibody. Ultimately, the rabbits are euthenized with pentobarbitol 150 mg/Kg IV. This and other procedures for raising polyclonal antibodies are disclosed in E. Harlow, et. al., editors, *Antibodies: A Laboratory Manual* (1988), which is hereby incorporated by reference. For instance, see Example 9 infra.

In addition to utilizing whole antibodies, the processes of the present invention encompass use of binding portions of such antibodies. Such antibody fragments can be made by conventional procedures, such as proteolytic fragmentation procedures, as described in J. Goding, *Monoclonal Antibodies: Principles and Practice*, pp. 98–118 (N.Y. Academic press 1983), which is hereby incorporated by reference.

The vaccines and passive immunization agents of this invention can be administered orally, parenterally, for example, subcutaneously, intravenously, intramuscularly, intraperitoneally, by intranasal instillation, or by application to mucous membranes, such as, that of the nose, throat, and bronchial tubes. They may be administered alone or with suitable pharmaceutical carriers, and can be in solid or liquid form such as, tablets, capsules, powders, solutions, suspensions, or emulsions.

The solid unit dosage forms can be of the conventional type. The solid form can be a capsule, such as an ordinary gelatin type containing the proteins or peptides of the present invention or the antibodies or binding portions thereof of the present invention and a carrier, for example, lubricants and inert fillers such as, lactose, sucrose, or cornstarch. In another embodiment, these compounds are tableted with conventional tablet bases such as lactose, sucrose, or cornstarch in combination with binders like acacia, cornstarch, or gelatin, disintegrating agents such as, cornstarch, potato starch, or alginic acid, and a lubricant like stearic acid or magnesium stearate.

The proteins or polypeptides of the present invention or the antibodies or binding portions thereof of this invention may also be administered in injectable dosages by solution or suspension of these materials in a physiologically acceptable diluent with a pharmaceutical carrier. Such carriers include sterile liquids such as water and oils, with or-without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions.

For use as aerosols, the proteins or polypeptides of the present invention or the antibodies or binding portions thereof of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

In yet another aspect of the present invention, the proteins or polypeptides of the present invention can be used as antigens in diagnostic assays for the detection of *Mycobacterium tuberculosis* body fluids. Alternatively, the detection of that bacillus can be achieved with a diagnostic assay employing antibodies or binding portions thereof raised by such antigens. Such techniques permit detection of *Mycobacterium tuberculosis* in a sample of the following tissue or body fluids: blood, spinal fluid, sputum, pleural fluids, urine, bronchial alveolor lavage, lymph nodes, bone marrow, or other biopsied materials.

In one embodiment, the assay system has a sandwich or competitive format. Examples of suitable assays include an enzyme-linked immunosorbent assay, a radioimmunoassay, a gel diffusion precipitan reaction assay, an immunodiffusion assay, an agglutination assay, a fluorescent immunoassay, a protein A immunoassay, or an immunoelectrophoresis assay.

In an alternative diagnostic embodiment of the present invention, the nucleotide sequences of the isolated DNA molecules of the present invention may be used as a probe in nucleic acid hybridization assays for the detection of *Mycobacterium tuberculosis* in various patient body fluids. The nucleotide sequences of the present invention may be used in any nucleic acid hybridization assay system known in the art, including, but not limited to, Southern blots (Southern, *J. Mol. Biol.*, 98: 503–17 (1975)(which discloses hybridization in 2×SSC (i.e. 0.15M NaCl, 0.015 sodium citrate), 40% formamide at 40° C.); Northern blots (Thomas et al., *Proc. Nat'l Acad. Sci. USA*, 77:5201–05 (1980)); Colony blots (Grunstein et al., *Proc. Nat'l Acad. Sci. USA*, 72:3961–65 (1975), which are hereby incorporated by reference). Alternatively, the isolated DNA molecules of the present invention can be used in a gene amplification detection procedure (e.g., a polymerase chain reaction). See H. A. Erlich et. al., "Recent Advances in the Polymerase Chain Reaction", *Science* 252:1643–51 (1991), which is hereby incorporated by reference.

More generally, the molecular basis for the uptake phenomenon achieved by *Mycobacterium tuberculosis* can be utilized to effect uptake of other materials into mammalian cells. This is achieved by utilizing the proteins or polypeptides of the present invention which effect cellular uptake (i.e. those proteins or polypeptides corresponding to the amino acids having SEQ. ID. Nos. 2 and 4) in association with such materials for uptake by mammalian cells. This phenomenon can be used to introduce a wide variety of materials into such cells, including antibiotics, DNA fragments, anti-neoplastic agents, and mixtures thereof.

The opportunity for direct cell entry of antibiotics constitutes a substantial advance, because they will be able to kill intracellular *Mycobacterium tuberculosis*. One approach for achieving such uptake is by impregnating microspheres with antibiotics and then coating the spheres with the cellular uptake proteins or polypeptides of the present invention in order to achieve such uptake. Alternatively, instead of utilizing microspheres to transport antibodies; such therapeutics can be chemically linked to the cellular uptake proteins or polypeptides of the present invention.

This technology can be used to treat a wide array of diseases caused by intracellular pathogens. For treatment of tuberculosis, a repertoire of antibiotics, having themselves poor cellular penetration but high activity against extracellular *Mycobacterium tuberculosis* when tested in vitro, can be utilized in conjunction with the cellular uptake proteins or polypeptides of the present invention. In cancer treatment, intracellular delivery of anti-neoplastic agents can be greatly enhanced by conjugating such agents to the cellular uptake proteins or polypeptides of the present invention. This will enable reductions in dosages for such agents and in their resulting toxicity.

Another aspect of the present invention is to utilize the cellular uptake proteins or polypeptides of the present invention in gene therapy or in a genetic vaccine where pieces of therapeutically or prophylactically useful DNA are conjugated at their thymine residues to these proteins or polypeptides of the present invention via linker arms. As a result, genetic material can be introduced into cells to correct genetic defects or to produce a desired characteristic or products that serve as immunogens.

EXAMPLES

Example 1

Preparation of and Screening for HeLa Cell Invasion Clones

To identify the *Mycobacterium tuberculosis* DNA sequence that encode mammalian cell entry, recombinant invasive clones were constructed as follows: *Mycobacterium tuberculosis* H37Ra strain (ATCC 25177) genome was digested with restriction enzymes Sau3 Al and Eco R1, and the DNA fragments were ligated into the Bam H1-Eco R1 restriction sites of a phagemid vector pBluescript II (Stratagene, La Jolla, Calif.). The recombinant vectors were introduced into *E. coli* EL1-Blue (Stratagene) by electroporation. We screened the recombinant strains for HeLa cell-invasive clones by a method similar to that described by R. R. Isberg and S. Falkow, *Nature* 317, 262 (1987), which is hereby incorporated by reference.

One *E. coli* transformant XL1-Blue(pZX7), which harbored a plasmid (pZX7) containing a 1535-base insert in the Bam HI-Eco RI restriction enzyme sites of the pBluescript vector, was found by the screening procedure to associate consistently with HeLa cells. It was confirmed by transmission electron microscopy that this clone entered HeLa cells (FIG. 1). FIG. 1A shows HeLa cells infected with *Mycobacterium tuberculosis* strain H37Ra (ATCC 25177), while the invasive recombinant strain *E. coli* XL1-Blue(pZX7) is shown in FIGS. 1B and 1C. The cells were incubated with *Mycobacterium tuberculosis* strain for 72 hours in FIG. 1A and with XL1-Blue(pZX7) for 7.5 hours in FIG. 1B and FIG. 1C. Internalization of this clone by HeLa cells was time-dependent (FIG. 1B), with intracellular organisms visible as early as 3.5 hours after infection. Some phagosomes contained multiple organisms (FIG. 1C), which suggested that the bacteria proliferated intracellularly. Some of the internalized bacilli were surrounded by a distinct ETZ, similar in appearance to the clear zone surrounding *Mycobacterium tuberculosis* inside HeLa cells (FIG. 1A, arrow). Whether this zone represents the ETZ often seen around other pathogenic intracellular mycobacterial organisms (See P. Draper and R. J. W. Rees, *Nature* 228, 860 (1970); N. Rastogi, *Res. Microbiol.* 141, 217 (1990); T. Yamamoto, M. Nishimura, N. Harada, T. Imaeda, *Int. J. Lepr.* 26, 111 (1958), which are hereby incorporated by reference) or is an artifact of the preparation is not clear.

Nonpathogenic *E. coli* XL1-Blue strains containing the vector pBluescript or another pBluescript-derived recombinant vector (pZN7) showed no association with HeLa cells after 7.5 hours.

To demonstrate that the invasive phenotype was indeed encoded by the cloned *Mycobacterium tuberculosis* DNA fragment, we transformed other nonpathogenic *E. coli* strains, specifically, HB101, DH5α, and NM522, with pZX7. The constructs HB101(pZX7), DH5α(pZX7), and NM522(pZX7) were invasive for HeLa cells. A spontaneous loss of pZX7 on prolonged storage of XL1-Blue(pZX7) was associated with loss of the invasive phenotype.

Four exonuclease III unidirectional deletion subclones of pZX7 and the subclones Bam HI-Pst I (pZX7.1), Pst-I-HinD III (pZX7.2), and Bam HI-Eco RI (pZx7.7) was utilized for HeLa cell association. The unidirectional deletion subclones of pZX7 were generated using exonuclease III according to the manufacturer's instruction (Erase-a-Base System, Promega, Madison, Wis.). The plasmid pZX7 was double-digested with HinD III and Kpn I restriction enzymes downstream from the Eco RI site of the Ban HI-Eco RI DNA insert to generate a 5' protruding end adjacent to the insert and a four-base 3' protruding end adjacent to the insert and a four-base 3' protrusion at the opposite strand to protect it from Exo III digestion. The digested plasmid was mixed with 300 U of Exo III at 37° C., and every 30 s 2.5 μl aliquots of the Exo III digestion were transferred to tubes containing S1 nuclease to remove the remaining single-stranded tails. The S1 nuclease was inactivated by neutralization and heating at 70° C. for 10 min. Klenow DNA polymerase was added to create blunt ends which were ligated to circularize the deletion-containing vectors. The ligation mixture was then used to transform the competent *E. coli* XL1-Blue strain by electroporation. These transformed strains were incubated for 6 hours with a HeLa cell monolayer.

Figure 2A:
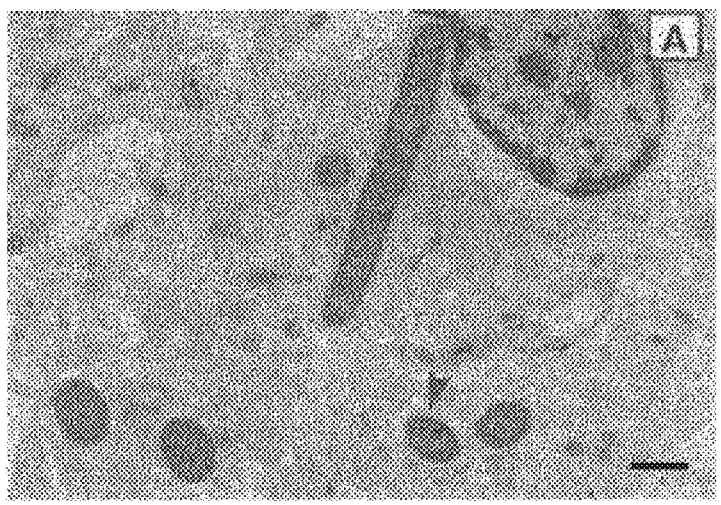
FIG. 2 shows the construction of unidirectional deletional subclones (pZX7.3, pZX7.4, pZX7.5, and pZX7.6) and Bam HI-Pst I (pZX7.1), Pst I-HinD III (pZX7.2), and Bam HI-Eco RI (pZX7.7) subclones from the original vector pZX7. The black bars represent the *Mycobacterium tuberculosis* DNA sequences, and the white bars represent pBluescript sequences. The subclone vectors were transferred into *E. coli* XL1-Blue and then incubated with these transformed strains for 6 hours with a HeLa cell monolayer.
Figure 2B:
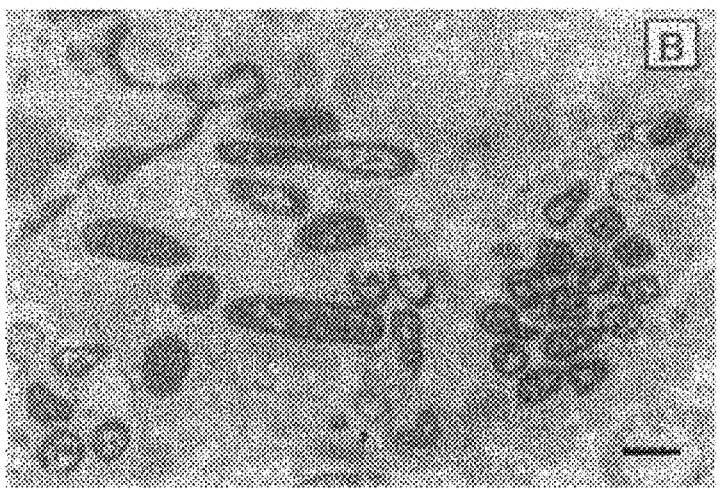
Figure 2C:

The results of this procedure are shown in FIG. 2. The black bars represent the *Mycobacterium tuberculosis* DNA sequences, and the white bars represent pBluescript sequences. As shown, the strains of *E. coli* XL1-Blue harboring pZX7.3, pZX7.4, or pZX7.5 associated with HeLa cells in a pattern similar to that for *E. coli* ZL1-Blue(pZX7), whereas the other subclones did not.

Example 2

Infection of Human Macrophages

Macrophage monolayers infected with the *E. coli* recombinant clones of Example 1 were established on glass cover slips at the bottom of polystyrene wells. They were initially infected with ~10 over-night-growth bacteria per macrophage cell for 1 or 2 hours followed by washing with phosphate-buffered saline (pH 7.4) and incubation for an additional 1, 6, or 22 hours. Cultures were performed at 37° C. in RPMI-1640 medium (Gibco) with 2% AB heat-inactivated human serum containing gentamicin (10 $\mu$g/ml). The gentamicin was included to kill the extracellular bacteria. The macrophage monolayer was washed again and then lysed with sterile, distilled water. The lysate was plated on tryptic soy agar medium to obtain colony counts. For microscopy, the macrophage monolayer was fixed with 100% methanol, stained with 10% Giemsa stain, and examined by light microscopy or processed for electron microscopy.

The monolayer that was infected for 1 hour only was examined by light microscopy immediately after it was washed, fixed, and stained. The macrophage lysate culture and light microscopy results are shown in Table 1, infra. The percentage of infected macrophages was calculated from counts of infected macrophages per 100 to 200 macrophage cells on a cover slip monolayer. Each *E. coli* strain was tested four to six times for each time point, and the means of the percentages of the cells infected by the *E. coli* recombinant clone and the control strains XL1-Blue (pBluescript) and XL1-Blue(pZX7.3) were compared by students T test.

FIG. 3 shows thin-section electron micrographs of human macrophages exposed to the invasive recombinant *E. coli* clone XL1-Blue(pZX7) for 3 hours (FIG. 3A) and 24 hours (FIG. 3B). In FIG. 3C, the thin-section micrograph is of human macrophages exposed to nonpathogenic *E. coli* XL1-Blue(pBluescript) for 24 hours. After 24 hours, bacilli were more numerous inside the cells, compartmentalized, surrounded by multiple layers of a membrane presumably of host origin (FIG. 3B). No bacteria could be seen inside macrophages infected with *E. coli* (pBluescript) after 24 hours (FIG. 3C).

Table 1 shows the results obtained from this light microscopy and culture study of human macrophage monolayer cells infected with the HeLa cell-invasive E. coli XL1-Blue (pZX7), subclone XL1-Blue (pZX7.3), and noninvasive XL1-Blue (p. Bluescript). The colony-forming units (CFU) were determined per milliliter of cell culture lysate. As shown, after 1 hour of infection, the percentage of cells infected by the recombinant clone (82±8%) was more than five times that of cells infected by XL1-Blue(pBluescript) (15±6%, P<0.001).

TABLE 1

| lysate Exposure (hours) | Percentage of infected cells (mean ± SEM) | | | CFU per milliliters of Culture (mean ± SEM) | |
|---|---|---|---|---|---|
| | pBluescript | pZX7.3 | pZX7 | pBluescript | pZX7 |
| 1 | 15 ± 6 | 59 ± 10** | 82 ± 8**** | ND***** | ND |
| 3 | 9 ± 4 | ND | 55 ± 17 | 1800 ± 500 | 3500 ± 1700 |
| 8 | 4 ± 2 | ND | 35 ± 5 | 10 ± 5 | 1600 ± 400 |
| 24 | 12 ± 10 | 23 ± 8* | 60 ± 13*** | 3 ± 1 | 1300 ± 200 |

*P > 0.05, compared with pBluescript clone. 0.001, compared with pBluescript or pZX7.3 clones. 0.05 compared with pZX7.3 clone.
**P > 0.001, compared with pBluescript clone.
***P > 0.001, compared with pBluescript or pZX7.3 clones.
****P > 0.0001, compared with pBluescript clone, P > 0.05 compared with pZX7.3 clone.
*****ND means not determined.

This observation suggests that the cloned *Mycobacterium tuberculosis* DNA sequences facilitate bacterial uptake at quantities above the background phagocytic activity of the macrophage cells. After 24 hours of infection, 12% (±10%) of the macrophages exposed to XL1-Blue(pBluescript) and 60% (±13%) of the cells exposed to XL1-Blue(pZX7) were infected (p <0.001). As demonstrated in Table 1, culture of the lysate of macrophages that had been infected for 24 hours showed that the intracellular *E. coli* XL1-Blue(pZX7) strains were viable.

In comparing capacity of XL1-Blue(pZX7), XL1-Blue (pBluescript), and one HeLa cell-invasive deletional derivative, *E. coli* XL1-Blue(pZX7.3), to infect macrophages from Table 1, at 1 hour of infection, the invasive capacity of *E. coli* XL1-Blue(pZX7.3) was four times that of XL1-Blue(pBluescript) (P<0.001), but by 24 hours the difference was no longer apparent. Thus, the DNA sequences associated with HeLa cell invasion are responsible for increased uptake by the macrophage, and the sequences that confer survival within the macrophage are located downstream of those necessary for mammalian cell entry.

Example 3

Homology Analysis

The Bam Hi-Eco Ri DNA fragment was sequenced by the chain termination method, described in F. Sanger, et. al., "DNA Sequencing with Chain-Terminating Inhibitors," *Proc. Nat. Acad. Sci.*, 74:5463–67, which is hereby incorporated by reference, and found to have 1535 base pairs [European Molecular Biology Laboratory (EMBL) accession number X70901]. The sequence showed no homology with any of the DNA sequences in the database of GenBank (R72.0) or EMBL (R31.0). No obvious procaryotic promoter consensus sequence could be discerned. If we assume that *Mycobacterium tuberculosis* uses the common prokaryotic termination codon sequences, amino acid sequence homologies can be identified. A region near the $NH_2$-terminus of the deduced sequence of one potential open reading frame was found to share (i) 27% identity with an 80-residue $NH_2$-terminus region of internalin, a protein encoded by Listeria monocytogenes that is associated with mammalian cell entry (A. B. Hartman, M. Venkatesan, E. V. Oaks, J. M. Buysse, *J. Bacteriol*, 172, 1905 (1990), which is hereby incorporated by reference); (ii) 20% identity with a 145-residue region of the IpaH gene product of the invasiveness plasmid of Shigella (B. E. Anderson, G. A. McDonald, D. C. Jones, R. L. Regnery, *Infect. Immun.* 58, 2760 (1990), which is hereby incorporated by reference); and (iii) 18% identity with a 176-residue region of human β-adaptin, a plasma membrane protein that links clathrin to receptors in coated vesicles which are responsible for receptor-mediated endocytosis (S. Ponnambalam, M. S. Robinson, A. P. Jackson, L. Peiper, P. Parham, *J. Biol. Chem.* 265, 4814 (1990) and J. L. Goldstein, M. S. Brown, R. G. W. Anderson, D. W. Russell, W. J. Schneider, *Annu. Rev. Cell Biol.* 1,1 (1985), which are hereby incorporated by reference). When aligned against the invasin protein of Yersinia pseudotuberculosis, the region associated with cell entry was 19% identical with a 100-residue region near the invasion COOH-terminus (R. R. Isberg, D. L. Voorhis, S. Falkow, *Cell* 50, 769 (1987), which is hereby incorporated by reference). The functional significance of these alignments is not clear.

Example 4

Functional Analysis of 52 kD Polypeptide

Protein fractions analyzed by SDS-polyacrylamide gel electrophoresis (SDS-PAGE) were prepared as follows: A 5-ml aliquot of bacterial overnight growth (adjusted to absorbance at 550 nm at optical density 600) in tryptic soy broth containing ampicillin (100 μg/ml) was harvested by centrifugation. We then sonicated the bacterial pellet in 1.5 ml of 10 mM tris-HCI buffer (pH 8.0) containing 5 mM $MgCl_2$. The sonicate was centrifuged for 25 min at 12,000 rpm in a microcentrifuge (Eppendorf model 5415C) at 4° C. Acetone was added to 600 μl of the supernatant in a fresh microcentrifuge tube (60% v/v), and the mixture was centrifuged for 25 min. at 14,000 rpm at 4° C. The pellet was resuspended in 20 μl of distilled water and 20 μl of Laemmli's boiling buffer, heated over boiling water for 5 min. and analyzed by SDS-PAGE. The bacterial debris containing the outer membrane fraction after the first centrifugation was resuspended in 100 μl of water and 100 μl of 15 mM tris-HCI buffer (pH 8.0) containing 7.5 mM $MgCl_2$ and 3% (v/v) Triton X-100 and centrifuged for 25 min. at 14,000 rpm. The pellet was resuspended in 25 μl of water and 25 μl of boiling buffer and boiled and analyzed a 20-μl aliquot of the sample by SDS-PAGE.

The SDS-PAGE (i.e., SDS-polyacrylamide gel electrophoresis) of acetone precipitated a soluble fraction of bacterial cell sonicate. The polypeptides were analyzed in a 9% gel (left): molecular size standards (lane 1), *E. coli* XL1-BBlue with a vector (pZN) containing an unrelated *Mycobacterium tuberculosis* DNA fragment between the Bam HI-Eco RI pBluescript cloning sites (lane 2), and XL1-Blue(pZX7) (land 3). Analysis in an 8% gel (right): XL1-Blue containing a vector (pZX7.8) with a two base frameshift introduced 12 bases upstream from the Bam HI cloning site in pZX7 (lane 1) and XL1-Blue(PZX7) (lane 2). Molecular sizes are indicated at the far right. We detected a 52-kD polypeptide in the soluble protein fraction of XL1-Blue(pZX7) (arrow). A protein of about 50 kD is expressed by XL1-Blue containing pZX7.8. The expression of the 52-kD protein was always associated with HeLa cell interaction of the recombinant *E. coli* clone.

Figure 4:
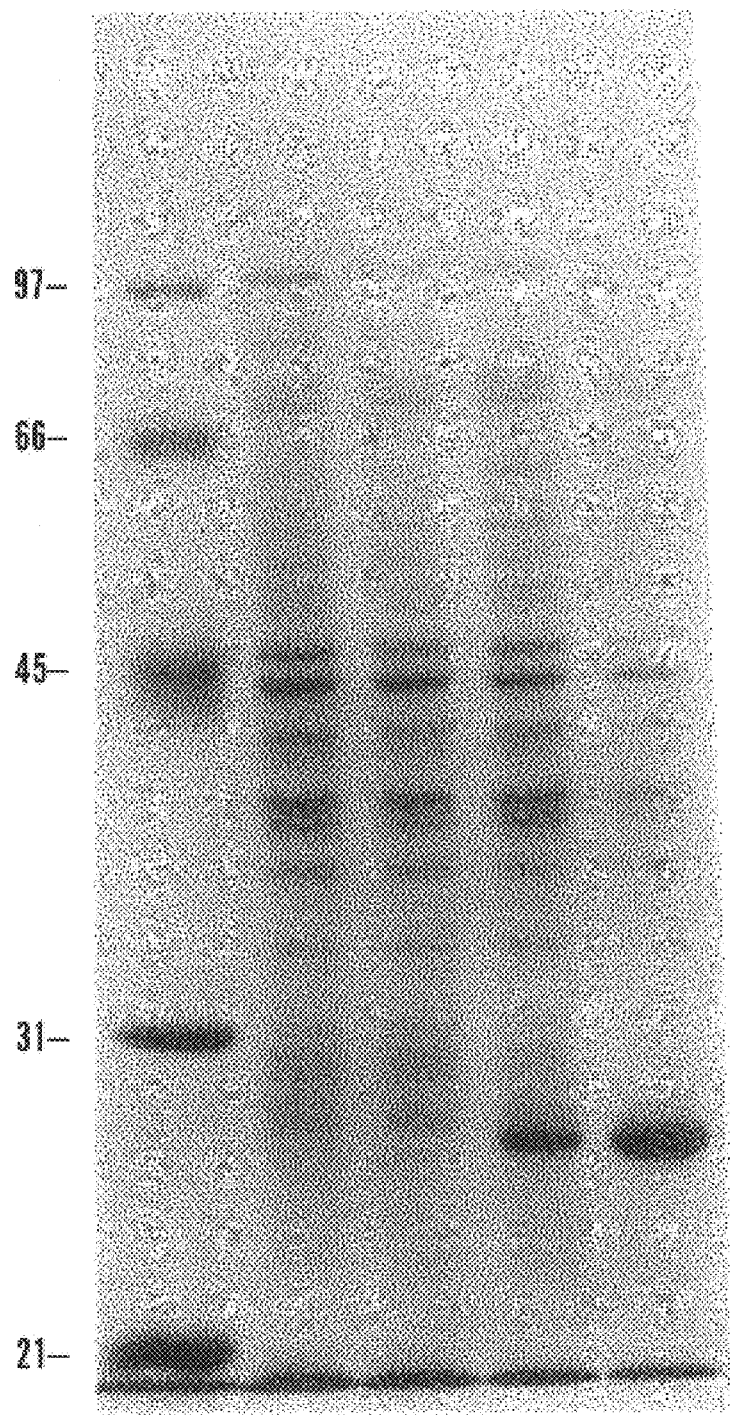
FIG. 4 shows the SDS-polyacrylamide gel electrophoresis of an acetone-precipitated soluble fraction of bacterial cell sonicate. The polypeptides were analyzed in a 9% gel (left): molecular size standards (lane 1), *E. coli* XL1-Blue with a vector (pZN7) containing an unrelated *Mycobacterium tuberculosis* DNA fragment between the Bam HI-Eco RI pBluescript cloning sites (lane 2), and XL1-Blue(pZX7) (lane 3). Analysis in an 8% gel (right): XL1-Blue containing a vector (pZX7.8) with a two-base frameshift introduced 12 bases upstream from the Bam HI cloning site in pZX7 (lane 1) and XL1-Blue(pZX7) (lane 2). Molecular sizes are indicated at the far right. We detected a 52-kD polypeptide in the soluble protein fraction of XL1-Blue(pZX7) (arrow). A protein of about 50 kD is expressed by XL1-Blue containing pZX7.8. The expression of the 52-kD protein was always associated with HeLa cell interaction of the recombinant *E. coli* clone.

From the SDS-PAGE results of FIG. 4, it can be concluded that a soluble fraction of the bacterial cell sonicate of XL1-Blue(pZX7) contained a 52-kD polypeptide that was not detected in the soluble fraction of XL1-Blue with a pBluescript-derived vector (pZN7) harboring an unrelated *Mycobacterium tuberculosis* DNA fragment. A two-base frameshift, introduced by blunt-end ligation after the 5' protruding end had been filled with Klenow DNA polymerase at the Xba I site 12 bases upstream from the Bam HI cloning site in pZX7 (confirmed by sequencing), led to loss of association with HeLa cells of the *E. coli* XL1-Blue containing this plasmid (pZX7.8). This clone did not express the 52-kD protein, but a new polypeptide of lower molecular mass was detected in the soluble fraction. A spontaneous loss of the capacity to associate with HeLa cells after prolonged storage of XL1-Blue(pZX7) was accompanied by loss of the 52-kD protein. Hence, this 52-kD protein is likely to be a product expressed by the cloned *Mycobacterium tuberculosis* DNA fragment. There were no detectable differences in the bacterial outer membrane polypeptide fractions.

Example 5

Subcloning the Open Reading Frame (ORF-1) that Encodes a Protein that Mediates Entry of *Mycobacterium Tuberculosis* into Mammalian Cells The nucleotide sequence corresponding to SEQ. ID. No. 3 (i.e. ORF-1) was subcloned into the EcoRI and HinDIIi endonuclease sites of pET vectors (pET23a, b, c, from Novagen). This was done by subcloning a PCR-amplified product of the ORF-1 fragment. The primers used to amplify the ORF-1 are as follows: EcoRI-primer: 5'-GGGGAATTCA TGTGAACGCC GACATCAA (SEQ. ID. No. 7); HinDIII-primer: 5'-GGGAAGCTTA TTGCG-GCAGC CCCGGCGTC (SEQ. ID. No. 8). Extracted DNA from *M. tuberculosis* strain H37Ra (ATCC 25177) was amplified for 30 cycles using the following PCR conditions: denaturation at 94° C. for 1 min, primer annealing at 56° C. for 2 min, and primer extension at 72° C. for 1 min. The amplified DNA was resolved by electrophoresis in 1.8% agarose gel, and, after visualization under UV illumination, the amplified DNA was removed from the gel using QIAEX, according to the manufacturer's instructions. The DNA was then digested with EcoRI and HinDIII in the same digestion buffer.

The pET vectors were also digested with EcoRI and HinDIII endonucleases, resolved in 1% agarose, and the linearized vector was removed from the gel, and mixed with the EcoRI/HinDIII digest of the PCR-amplified ORF-1 DNA fragment for a ligation reaction.

The ligation reaction was performed as follows: To a mixture containing 5 μl of the digested PCR-amplified DNA product and 3 μl of the vector DNA digest, 1 μl of 10X T4 ligase buffer (New England BioLabs) and 1 μl of T4 ligase (15 U) were added. The mixture was incubated at room temperature for 4 hrs. A 1.5 μl aliquot of the ligation mixture was electroporated into *E. coli* strain BL21 (DE3), and the *E. coli* was inoculated onto ampicillin-containing (200 μg/ml) agar plates for incubation overnight at 37° C. Representative colonies from each of the pET23 constructs (pET23a-ORF1, pET23b-ORF1, pET23c-ORF1) were tested for their association with HeLa cells as described elsewhere. The strains were tested with and without induction by IPTG.

Example 6

SDS-Polyacrylamide Gel Electrophoresis Analysis Of The Protein Expressed By ORF-1

To express the protein encoded by ORF-1, the pET23 recombinant BL21 (DE3) *E. coli* strains were first grown overnight in 5 ml of ampicillin containing tryptic soy broth (TSB) medium. The following day, a 500-μl sample was pelleted and resuspended in 5 ml of TSB containing ampicillin (200 μg/ml), and incubated for 3 hrs. Then, 50 μl of IPTG (40 mM) was added to the growth and incubated for additional 2 hrs at 37C. A 1-ml bacterial suspension (OD= 500 at $AbS_{600}$) was pelleted, and the pellet was resuspended in 50 μl water and 50 μl of Laemmli's boiling buffer and boiled for 5 min. A 15 μl-aliquot of the boiled sample was loaded onto 12% SDS-polyacrylamide gel, and resolved electrophoretically. BL21 (DE3) containing a pET vector was treated similarly as a control in these experiments.

Figure 5A:
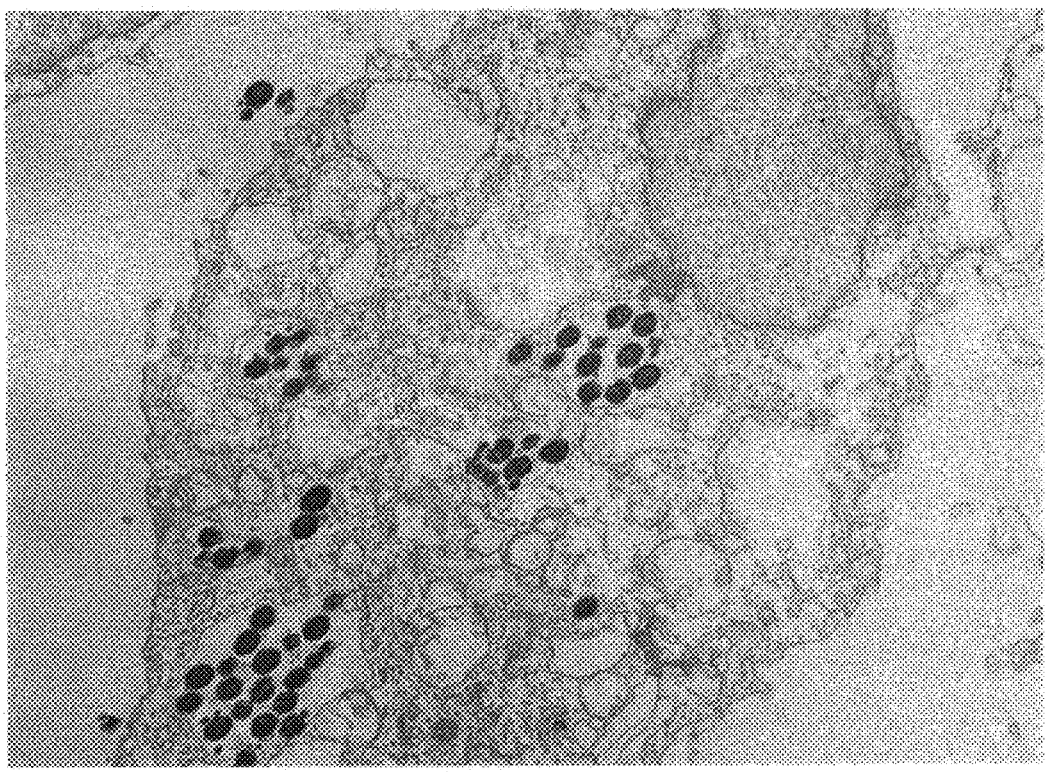
FIG. 5 shows an SDS-PAGE analysis of recombinant *E. coli* lysates with the low molecular weight marker in lane 1, *E. coli* BL21 (DE3) in lane 2, *E. coli* BL21 (DE3)(pET23c) in lane 3, *E. coli* BL21 (DE3)(pET23c-ORF1), uninduced in lane 4, and *E. coli* BL21 (DE3) (pET23c-ORF1) induced in lane 5.
Figure 5B:
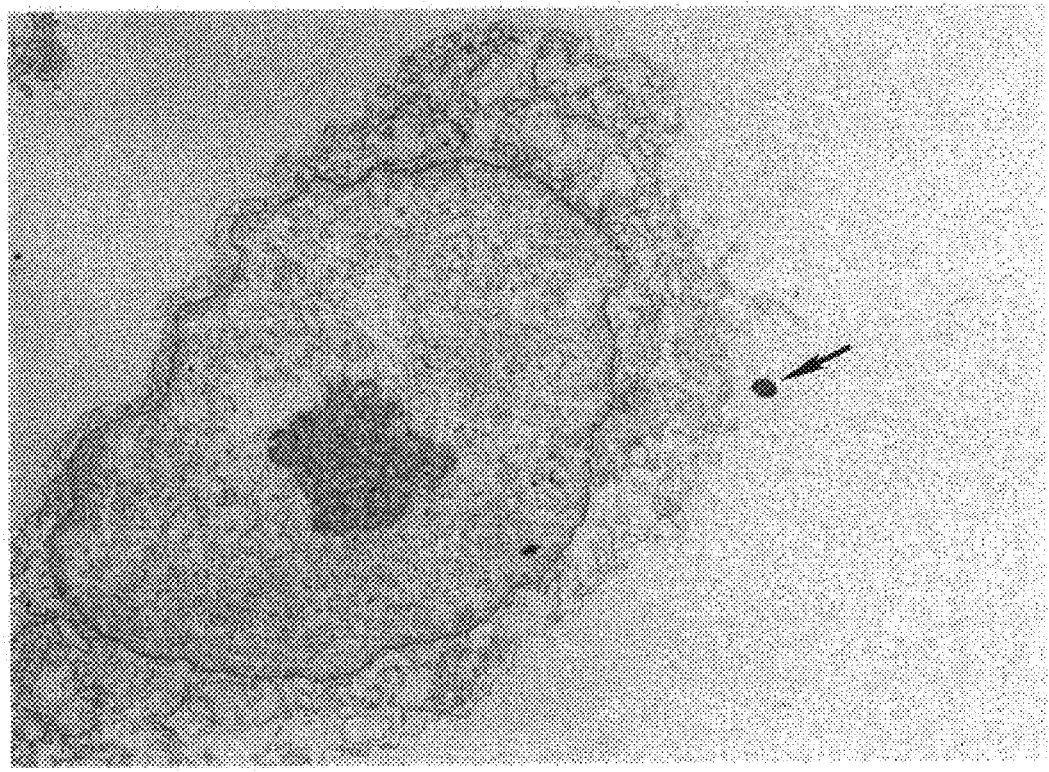

The SDS-PAGE revealed a protein at position around 25–28 KDa expressed by BL21 (DE3)(pET23c-ORF1), that was not expressed by any of the other pET23 constructs or the control BL21 (DE3) (pET23c) strain. Even without induction by IPTG, some expression of the protein was evident (FIG. 5). The same recombinant strain BL21 (DE3) (pET23c-ORF1) showed a strong association with HeLa cells also. Hence, the expressed product of ORF-1 has been shown to be sufficient to confer HeLa cell association.

Example 7

N-terminal Analysis of the Recombinant ORF-1 Protein

The IPTG-treated BL21 (DE3)(pET23c-ORF1) strain was prepared as described above for SDS-PAGE. Eight lanes were loaded with the same bacterial lysate, and one lane was loaded with the control E. coli lysate. After electrophoresis, the resolved proteins were transferred onto a piece of PVDF membrane (Immobilon, Millipore), using an electro-blotting apparatus (IDEA Scientific Company). The membrane was stained with Coomassie Blue for 2 min and destained until the transferred protein bands became visible. A protein fraction of 25–28 KDa in the recombinant E. coli lanes, not present in the control E. coli lane, was cut out, and sent to Stanford University Protein and.Nucleotide Facility for microsequencing of the N-terminus. The N-terminus contained the pET vector's T7 tag amino acid sequence (position 1 to 15), followed by Val, Asn, Ala, Asp, Ile, which confirms the N-terminus amino acid sequence deduced from the nucleotide sequence of ORF-1.

Example 8

Coating of Latex Beads with the Recombinant Protein to Study HeLa Cell Association of the Beads A crude preparation of the 25–28 kDa protein encoded by ORF-1 was obtained from BL21 (DE3)(pET23c-ORF1) as follows: The protein was expressed as described above by IPTG induction. After induction, the bacterial suspension was mixed to a final concentration of 10% (vol/vol) in a Tris buffer (pH 8.0) containing 100 mM NaCl and 1 mM EDTA. Lysozyme was added to the solution to a final concentration of 1 mg/ml, and the cells were incubated at room temperature for 20 min. The cells were then centrifuged at 5000 g for 10 min, and the supernatant was discarded. The pellet was transferred to ice, and resuspended in 5 ml of ice-cold 50 mM Tris buffer (pH 8.0) containing 100 mM NaCl, 1 mM EDTA, and 0.1% sodium deoxycholate. $MgCl_2$ and DNAseI were added to final concentrations of 8 mM and 10 μg/ml, respectively. Incubation was carried out on ice until the viscocity disappeared. The inclusion body constituting the material in the suspension was removed by centrifugation at 10,000 g for 10 min. The resulting pellet was washed by resuspending in 5 ml of 50 mM Tris buffer containing 1% NP-40, 100 mM NaCl, and 1 mM EDTA, followed by washing in the same buffer not containing NP-40. An aliquot of the pellet material was examined by SDS-PAGE for the presence of the recombinant protein.

The remainder of the pellet was dissolved in 2 ml of 6 M guanidium-HCL (GuHCl) in a 25 mM HEPES buffer (pH 7.6) containing 100 mM KCl, 0.1 mM EDTA, 125 mM $MgCl_{21}$ 10% glycerol, and 0.1% NP-40 (HEMGN buffer), that contained protease inhibitors (1 mM DTT, 2 μg/ml aprotinin, 1 μg/ml leupeptin, 1 μg/ml pepstatin, 0.1 mM PMSF, and 0.1 mM Na-metabisulfite). The solubilized protein was subjected to sequential dialysis against the HEMGN buffer lacking 6 M GuHCl at 4C over a period of 2 days. For control, the same procedure was carried out with the cells of E. coli BL21 (DE3) (pET23c). The protein concentration was determined by the BCA protocol.

A 2-μl sample of 10% aqueous suspension of 0.3 μm polystyrene latex beads (Sigma) was added to 1 ml of 100 μg/ml protein solution in PBS (pH 7.5). The beads were incubated with the protein solution overnight at 37C with constant shaking, and subjected to periodic, brief sonication to disperse the clumps. A 100-μl suspension of the beads was then added to HeLa cell monolayers grown in MEM (containing 10% fetal calf serum) on round glass coverslips in 24-well tissue culture plates. The controls included beads incubated in PBS alone, in PBS containing 1% BSA, and beads coated with the protein preparation from the control E. coli strain described above. The HeLa cell monolayers in 2 ml of MEM per well were incubated for 5 hrs at 37 C, then washed 5 times with PBS, and fixed with 100% methanol for 30 min. The cells were then stained with 10% Giemsa for 20 min and examined by light microscope.

HeLa cells were also prepared for examination by transmission electron microscopy. The HeLa cell monolayers after the 5-hr incubation period were fixed in 2% glutealdehyde in PBS (pH 7.5) for 3 hrs, then scraped off, and resuspended in the same glutealdehyde buffer. The cells were then gently pelleted, and the pellet was prepared for sectioning by a standard protocol for transmission electron microscopy. One result is shown in FIG. 6.

Example 9

Raising a Polyclonal Antisera to the Recombinant Protein

A lysate of E. coli BL21 (DE3) (pET23c-ORF1) expressing the 25–28 kDa protein was resolved by 12% SDS-PAGE in multiple wells, and the protein was excised from the gel. The pieces of acrylamide gel containing the protein was then pulverized using a mortar and pestle, and resuspended in 2 ml of sterile PBS (pH 7.5). A rough estimate of the protein concentration was made by the BCA method. Six-month-old NZW female rabbits were injected subcutaneously at 7–8 sites with approximately 20 μg of the antigen suspension per site. The rabbits were boosted with the same amount of antigen after 4 weeks and 6 weeks of the first injection. Serum was collected from blood obtained after 2 weeks of the last booster injection. Its reactivity to the recombinant protein was examined by Western blotting. The immune antiserum diluted 1:10,000 was able to detect less than 1 μg of the protein bound to nitrocellulose membrane. Both the 52 Kilodalton polypeptide of Example 4 and the 23–28 Kilodalton polypeptide of Example 7 were recognized by these antibodies.

Example 10

Analysis for the Presence of IS6110

A partial digest of the genomic DNA of Mycobacterium tuberculosis strain H37Ra (ATCC 25177) was prepared with Sau3AI and EcoRI restriction enzymes. Because the H37Ra strain contains multiple copies of IS6110, described by U.S. Pat. No. 5,183,737 to Crawford, et al., and IS6110 does not have an EcoRI site, the digest would contain several DNA fragments containing IS6110. The DNA fragments were ligated into the BamHI-EcoRI restriction sites of the vector pBluescript II to create a recombinant library. The recombinant vectors were then electroporated into *E. coli* XL1-Blue. These recombinant *E. coli* strains were then screened for invasive clones by the method described elsewhere in this application.

After the initial screening using HeLa cells, *E. coli* colonies were recovered. Only one of these consistently showed association with HeLa cells. This is the previously described strain XL1-Blue (pZX7). Others showed either weak or no association with HeLa cells when tested multiple times. These other strains were recently tested for the presence of IS6110 by a probe generated from PCR-amplification of a 245-bp region within IS6110 using the following primers: INS1: 5'-CGTGAGGGCATCGAGGTGGC (SEQ. ID. No. 9) and INS2: 5'-GCGTAGGCGTCGGTGACAAA (SEQ. ID. No. 10).

None contained the IS6110 sequences. Furthermore, the absence of consistent and strong association of other clones with HeLa cells suggests that the sequence contained within pZX7 is the only sequence among the DNA fragments in this genomic library that encodes mammalian cell entry.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. An isolated DNA molecule encoding a Mycobacterium protein and conferring on *Mycobacterium tuberculosis* an ability to enter mammalian cells and to survive within macrophages, wherein said DNA molecule encodes an amino acid sequence corresponding to SEQ. ID. No. 2.

2. An isolated DNA molecule according to claim 1, wherein said DNA molecule encodes for the polypeptide having a molecular weight of about 50–55 kilodaltons.

3. An isolated DNA molecule encoding a Mycobacterium protein and conferring on *Mycobacterium tuberculosis* an ability to enter mammalian cells, wherein said DNA molecule encodes an amino acid sequence corresponding to SEQ. ID. No. 4.

4. An isolated DNA molecule according to claim 3, wherein said DNA molecule encodes for a polypeptide having a molecular weight of about 22 to 28 kilodaltons.

5. An isolated DNA molecule encoding a Mycobacterium protein and conferring on *Mycobacterium tuberculosis* an ability to survive within macrophages, wherein said DNA molecule encodes an amino acid sequence corresponding to SEQ. ID. No. 6.

6. A recombinant DNA expression system comprising a DNA molecule according to claim 1.

7. A recombinant DNA expression system comprising a DNA molecule according to claim 3.

8. A recombinant DNA expression system comprising a DNA molecule according to claim 5.

9. A recombinant DNA expression system according to claim 6, wherein said DNA is inserted into said expression system in proper orientation and correct reading frame.

10. A host cell comprising a heterologous DNA molecule according to claim 1.

11. A host cell comprising a heterologous DNA molecule according to claim 3.

12. A host cell comprising a heterologous DNA molecule according to claim 5.

13. An isolated DNA molecule encoding a Mycobacterium protein or polypeptide and conferring on *Mycobacterium tuberculosis* an ability to enter mammalian cells and to survive within macrophages, wherein said DNA molecule comprises a nucleic acid sequence which hybridizes to the nucleotide sequence corresponding to SEQ. ID. No. 1 when hybridization is performed in 2×SSC, 40% formamide at 40° C.

14. An isolated DNA molecule encoding a Mycobacterium protein or polypeptide and conferring on *Mycobacterium tuberculosis* an ability to enter mammalian cells, wherein said DNA molecule comprises a nucleic acid sequence which hybridizes to the nucleotide sequence corresponding to SEQ. ID. No. 3 when hybridization is performed in 2×SSC, 40% formamide at 40° C.

15. An isolated DNA molecule encoding a Mycobacterium protein or polypeptide and conferring on *Mycobacterium tuberculosis* an ability to survive within macrophages, wherein said DNA molecule comprises a nucleic acid sequence which hybridizes to the nucleotide sequence corresponding to SEQ. ID. No. 5 when hybridization is performed in 2×SSC, 40% formamide at 40° C.

16. A recombinant DNA expression system comprising a DNA molecule according to claim 13.

17. A recombinant DNA expression system comprising a DNA molecule according to claim 14.

18. A recombinant DNA expression system comprising a DNA molecule according to claim 15.

19. A host cell comprising a heterologous DNA molecule according to claim 13.

20. A host cell comprising a heterologous DNA molecule according to claim 14.

21. A host cell comprising a heterologous DNA molecule according to claim 15.

22. An isolated DNA molecule according to claim 1, wherein said DNA molecule comprises a nucleotide sequence corresponding to SEQ. ID. No. 1.

23. An isolated DNA molecule according to claim 3, wherein said DNA molecule comprises a nucleotide sequence corresponding to SEQ. ID. No. 3.

24. An isolated DNA molecule according to claim 5, wherein said DNA molecule comprises a nucleotide sequence corresponding to SEQ. ID. No. 5.

* * * * *